United States Patent
Simpkins

(10) Patent No.: US 12,036,321 B2
(45) Date of Patent: Jul. 16, 2024

(54) COMPOSITIONS AND METHODS FOR TREATING OR PREVENTING MULTIPLE ORGAN DYSFUNCTION SYNDROME

(71) Applicant: VIVACELLE BIO, INC., Shreveport, LA (US)

(72) Inventor: Cuthbert O. Simpkins, Shreveport, LA (US)

(73) Assignee: VIVACELLE BIO, INC., Shreveport, LA (US)

( * ) Notice: Subject to any disclaimer, the term of this patent is extended or adjusted under 35 U.S.C. 154(b) by 37 days.

(21) Appl. No.: 17/934,112

(22) PCT Filed: Apr. 2, 2021

(86) PCT No.: PCT/US2021/070351
§ 371 (c)(1),
(2) Date: Sep. 21, 2022

(87) PCT Pub. No.: WO2021/203143
PCT Pub. Date: Oct. 7, 2021

(65) Prior Publication Data
US 2024/0009126 A1    Jan. 11, 2024

Related U.S. Application Data

(60) Provisional application No. 63/004,769, filed on Apr. 3, 2020.

(51) Int. Cl.
*A61K 9/127* (2006.01)
*A61P 43/00* (2006.01)
(52) U.S. Cl.
CPC ............. *A61K 9/127* (2013.01); *A61P 43/00* (2018.01)

(58) Field of Classification Search
CPC ....................................................... A61K 9/127
USPC ........................................................ 424/450
See application file for complete search history.

(56) References Cited

FOREIGN PATENT DOCUMENTS

| WO | 01/03669 A2 | 1/2001 |
|---|---|---|
| WO | 2010/081862 A2 | 7/2010 |
| WO | 2017/048792 A1 | 3/2017 |
| WO | 2017/222912 A1 | 12/2017 |

OTHER PUBLICATIONS

International Search Report, mailed Jun. 22, 2021, in corresponding International Application No. PCT/US2021/070351.

Written Opinion of the International Searching Authority, mailed Jun. 22, 2021, in corresponding International Application No. PCT/US2021/070351.

*Primary Examiner* — Raymond J Henley, III
(74) *Attorney, Agent, or Firm* — Michael Ye; Kalos Athena Wang PLLC

(57) ABSTRACT

A PN composition for treating multiple organ dysfunction syndrome (MODS) comprises a lipophilic or hydrophobic component, an amphiphilic emulsifier, a polar liquid carrier, and one or more electrolytes, where the amphiphilic emulsifier forms micelles having a lipophilic or hydrophobic core comprising the lipophilic or hydrophobic component in the polar liquid carrier, and/or liposomes organized as a lipid bilayer and/or other particle configurations. This is a PN composition that takes up nitric oxide and releases it with enhanced rapidity enabling it to shift the balance of nitric oxide from one that exacerbates organ damage and decreased survivability to one that reverses and/or inhibits organ damage and increases survivability.

13 Claims, 1 Drawing Sheet

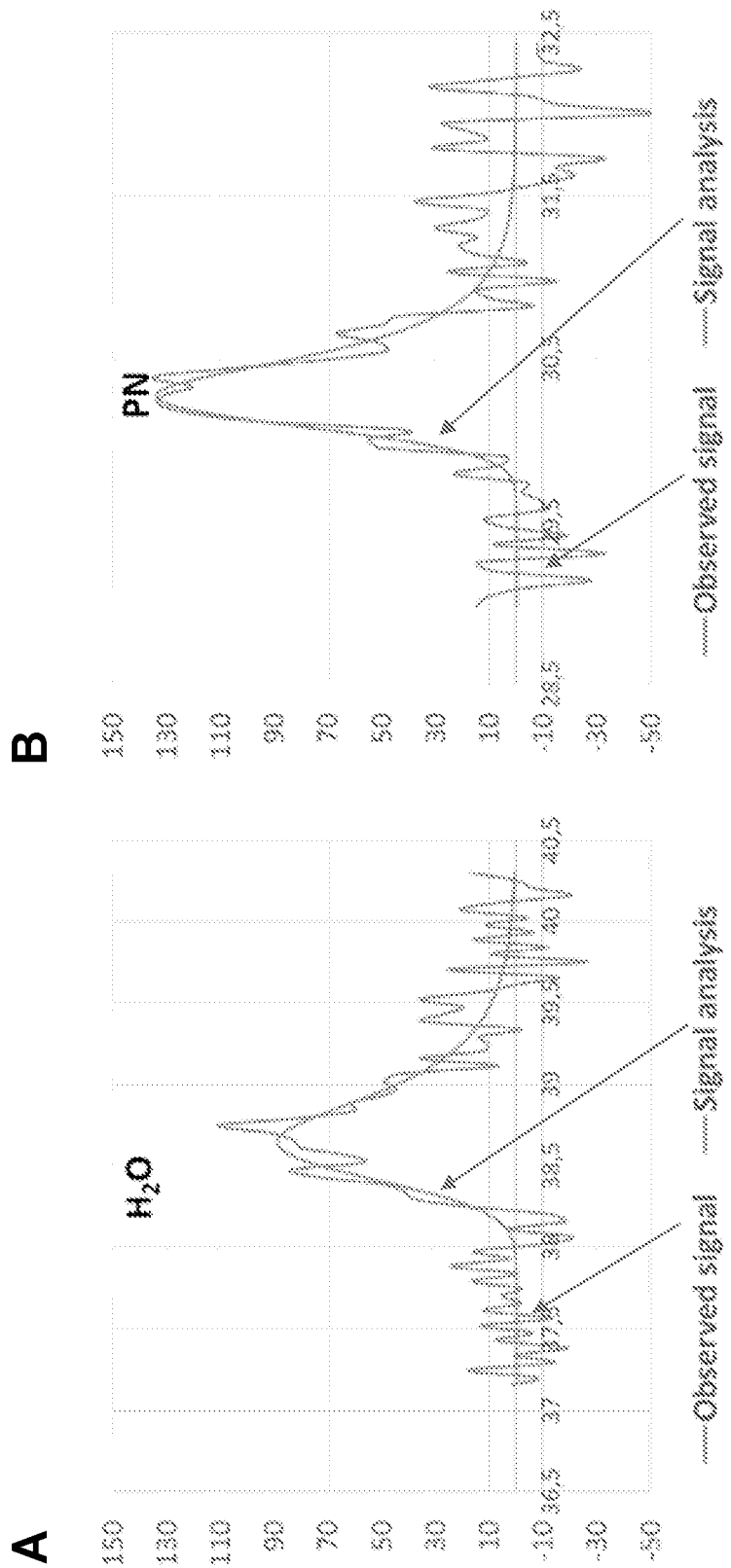

COMPOSITIONS AND METHODS FOR TREATING OR PREVENTING MULTIPLE ORGAN DYSFUNCTION SYNDROME

RELATED APPLICATIONS

This application claims priority of U.S. Provisional Application No. 63/004,769, filed on Apr. 3, 2020. The entirety of the aforementioned application is incorporated herein by reference.

FIELD

The technical field is medical treatment and, in particular, methods and compositions for treating multiple organ dysfunction syndrome (MODS).

BACKGROUND

Multiple Organ Dysfunction Syndrome (MODS) is the failure of multiple organs of the body requiring intensive medical intervention. MODS is the leading cause of morbidity and mortality in current ICU practice. MODS is triggered by a wide variety of causes such as major trauma, burns, eclampsia, sepsis, pancreatitis, aspiration syndromes, extracorporeal circulation (e.g. cardiac bypass), multiple blood transfusion, ischemia-reperfusion injury, autoimmune disease, heat-induced illness, or poisoning/toxicity. MODS is strongly associated with widespread inflammation. However, anti-inflammatory agents have failed to show efficacy in treating MODS. A definite unitary cause of MODS has not been revealed.

Management of MODS seeks to address the initiating cause and to provide intensive support specific to the failure of each vital organ. The lungs are supported with ventilators and increased delivery of oxygen to the lungs. The kidney s are supported with dialysis. The heart is supported with pharmacological agents or devices that augment cardiac output. Outside of possible extant experimental protocols there is no routine support for liver failure at this time.

Some of the attempts to reverse the vascular system failure have focused on treating low blood pressure (hypotension) and/or reducing high concentrations of nitric oxide (NO), which are typically found in patients with septic shock. Overproduction of NO causes vasodilation and a decrease in blood pressure. However, increasing the blood pressure alone does not automatically lead to an improvement in the other organ systems. In fact, administration of Levophed, a vascoconstrictor for treating life-threatening low blood pressure (hypotension) is known to actually worsen organ damage. Similarly, an attempt to treat patients with septic shock with the nitric oxide synthase inhibitor 546C88 was unsuccessful and actually led to increased mortality and multiple organ failure.

In patients with MODS, the responsiveness of the blood to vasopressor medications that constrict the blood vessels and raise blood pressure is markedly decreased. In addition, cardiac contractility is decreased. Other vasoactive active medications such as dobutamine that increases cardiac contractility or other medications that act via other mechanisms also fail to reverse the adverse effects of MODS. When patients die, they have lost their responsiveness to vasopressor medications and their blood pressure decreases to an unsurvivable level.

In view of the foregoing, there is a need for a treatment that improves organ function in patients with MODS. The inventors of the present application have unexpectedly found that administration of a phospholipid nanoparticle (PN) composition can present or reduce multiple organ dysfunction syndrome.

SUMMARY

An aspect of the application is a method for reducing or preventing multiple organ dysfunction syndrome (MODS) in a subject in need thereof. The method comprises the step of administering to a subject in need of the treatment, an effective amount of a phospholipid nanoparticle (PN) composition comprising: a lipophilic or hydrophobic component in an amount of 0-35% (w/v); an amphiphilic emulsifier in an amount of 0.1%-60% (w/v); a polar liquid carrier; and one or more electrolytes, wherein the PN composition comprises liposomes and/or micelles having a mean diameter of 1-500 nm. In some embodiments, the PN composition comprises the lipophilic or hydrophobic component and the amphiphilic emulsifier in a total amount of 10-50% (w/v).

Another aspect of the application is a method for treating multiple organ dysfunction syndrome (MODS) in a subject, comprising, administering to a subject in need of treatment, an effective amount of a phospholipid nanoparticle (PN) composition comprising: a lipophilic or hydrophobic component in an amount of 0-35% (w/v); an amphiphilic emulsifier in an amount of 0.6%-60% (w/v); a polar liquid carrier; and one or more electrolytes, wherein the PN composition comprises liposomes and/or micelles having a mean diameter of 1-500 nm. In some embodiments, the PN composition comprises the lipophilic or hydrophobic component and the amphiphilic emulsifier in a total amount of 10-50% (w/v).

In certain embodiments, the lipophilic or hydrophobic component is selected from the group consisting of soybean oil, chia bean oil, algae oil and silicone oil.

In certain embodiments, the amphiphilic emulsifier is selected from the group consisting of phospholipids and α-phosphatidylcholine. In particular embodiments, the amphiphilic emulsifier is selected from the group consisting of egg yolk lecithin, soy bean lecithin and amphiphilic peptides.

In certain embodiments, the polar liquid carrier is selected from the group consisting of water, a water-based solution and a non-aqueous polar liquid.

In certain embodiments, the non-aqueous polar liquid is selected from the group consisting of dimethyl sulfoxide, polyethylene glycol and polar silicone liquids.

In certain embodiments, the electrolytes are selected from the group consisting of one or more of sodium chloride, sodium hydrogen carbonate, sodium citrate, sodium lactate, sodium sulfate, sodium dihydrogen phosphate, disodium hydrogen phosphate, sodium acetate, sodium glycerophosphate, sodium carbonate, an amino acid sodium salt, sodium propionate, sodium hydrotybutyrate, sodium gluconate, potassium chloride, potassium acetate, potassium gluconate; potassium hydrogen carbonate, potassium glycerophosphate, potassium sulfate, potassium lactate, potassium iodide, potassium dihydrogen phosphate, dipotassium hydrogen phosphate, potassium citrate, an amino acid potassium salt, potassium propionate, potassium hydroxy butyrate, calcium chloride, calcium gluconate, calcium lactate, calcium gly cerophosphate, calcium pantothenate, calcium acetate, magnesium chloride, magnesium sulfate, magnesium glycerophosphate, magnesium acetate, magnesium lactate, an amino acid magnesium salt, ammonium chloride, zinc sulfate, zinc chloride, zinc gluconate, zinc lactate, zinc acetate, iron sulfate, iron chloride, iron gluconate, copper sulfate, and manganese sulfate.

In certain embodiments, the PN composition has a concentration of potassium ion in a subphysiological range of between 2-3 mEq/l K+(2-3 mM).

In certain embodiments, the PN composition has a concentration of magnesium ion in a subphysiological range.

In certain embodiments, the PN composition comprises micelles and liposomes, wherein the micelles in the PN composition have a mean diameter in the range of 30-450 nm as measured by electron microscopy and wherein the liposomes in the PN composition have a mean diameter in the range of 1-25 nm as measured by electron microscopy. In certain embodiments, the PN composition comprises micelles and liposomes, wherein the micelles in the PN composition have diameters in the range of 15-800 nm as measured by electron microscopy and wherein the liposomes in the PN composition ha % e diameters in the range of 1-300 nm as measured by electron microscopy.

In certain embodiments, the PN composition is administered either intravenously, intra-arterially, intraosseously or intracardially.

In certain embodiments, the PN composition is an oxygenated PN composition with an oxy gen content of 1-50 ml $O_2$/100 mi PN composition.

In certain embodiments, the PN composition has an emulsifier lipophilic or hydrophobic component ratio (w/w) between about 1:200 to about 1:1. In certain embodiments, the PN composition has an emulsifier:lipophilic or hydrophobic component ratio (w/w) between about 1:200 to about 1:1.7.

In certain embodiments, the PN composition further comprises a crystalloid agent.

In certain embodiments, the PN composition further comprises an oncotic agent.

In certain embodiments, the PN composition further comprises an anti-inflammatory or immunomodulatory agent.

In certain embodiments, the PN composition further comprises a lipophilic gas.

In certain embodiments, the subject has MODS induced by sepsis caused by flu virus or coronavirus infection. In certain embodiments the subject has MODS induced by sepsis caused by one or more from the group consisting of major trauma, burns, eclampsia, sepsis, pancreatitis, aspiration syndromes, extracorporeal circulation, cardiac bypass, multiple blood transfusion, ischemia-reperfusion injury, autoimmune disease, heat-induced illness, and poisoning/toxicity.

Another aspect of the application is a method for treating multiple organ dysfunction syndrome (MODS) in a subject, comprising: administering to a subject in need of treatment, an effective amount of a phospholipid nanoparticle (PN) composition comprising soy bean oil in an amount of 5%-35% (w/v); lecithin in an in an amount of 0.5%-15% (w/v), sodium chloride and sodium lactate as electrolytes, wherein the total electrolyte composition is between 50 mM to 200 mM; histidine in an amount between 0.001 mM to 10 mM, and water, wherein the lecithin forms, (1) lipid-carrying micelles having a lipophilic or hydrophobic core in an aqueous solution and the resulting micelles have a mean diameter in the range of 30-500 nm as determined by electron microscopy, and wherein said lipid-carrying micelles are stable for at least 4 weeks at room temperature, and (2) liposomes having a mean diameter in the range of 1-500 nm, as determined by electron microscopy. In certain embodiments, the PN composition further comprises ox % gen.

BRIEF DESCRIPTION OF DRAWINGS

FIG. 1 shows the uptake of nitric oxide by w % ater (panel A) and a PN composition (panel B) measured by mass spectroscopy.

DETAILED DESCRIPTION

Reference will be made in detail to certain aspects and exemplary embodiments of the application, illustrating examples in the accompanying structures and figures. The aspects of the application will be described in conjunction with the exemplary embodiments, including methods, materials and examples, such description is non-limiting and the scope of the application is intended to encompass all equivalents, alternatives, and modifications, either generally known, or incorporated here. Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present application. The described aspects and embodiments of the application are not limited to the methods and materials described.

As used in this specification and the appended claims, the singular forms "a," "an" and "the" include plural referents unless the content clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

The term "acute critical illness", is meant to include any condition rendering the patient in immediate need for intensive care therapy. The condition may be caused by am acute and extensive injurious hit to the body including but not limited to physical trauma, burn injury trauma, infection (hereunder sepsis, severe sepsis, septic shock), systemic inflammatory response syndrome (SIRS), acute myocardial infarction or other thromboembolic events.

The term "intensive care therapy", also term "organ supportive care" here, may include but is not limited to ventilation therapy, (e.g., mechanical ventilation), hemodialysis, vasopressor therapy, fluid therapy, blood transfusion therapy with administration of red blood cell concentrates, fresh frozen plasma, platelet concentrates. Whole blood or coagulation factor concentrates, systemic antibiotic and/or antiviral and/or antifungal and/or antiprotoioic therapy, parenteral nutrition, granulocyte infusion, T cell infusion, stem cell infusion, anticoagulant and/or antithrombotic therapy including to molecular ((eight heparins, administration of corticosteroids, tight glycemic control etc.

The term "trauma" as used herein means any shock or body wound produced by a sudden physical injury such as accident, injury or impact to living tissue caused by an extrinsic agent such as blast trauma, blunt trauma, penetrating trauma, trauma caused by chemical injury (spills, warfare or intoxication), radiation or burns.

The term "shock" is used in the conventional clinical meaning, i.e. shock is a medical emergency in which the organs and tissues of the body are not receiving an adequate flow of blood. This deprives the organs and tissues of oxygen (carried in the blood) and allows the build-up of waste products. Shock is caused by five major categories of problems, cardiogenic (meaning problems associated with the heart's functioning):

hypovolemic/hemorrhagic (meaning that the total volume in the intravascular space is low due to loss of fluid from the intravascular space or dilation of blood vessels so that the volume of fluid in the circulatory system is low in an absolute or relative sense), neurogenic (caused by severe injure to the central nervous system), septic (caused by overwhelming infection, usually by bacteria) or anaphylactic/allergic (caused by systemic histamine release from immune cells and excessive vasodilation).

As used herein, the terms "treatment" and "treating" refer to the management and care of a patient with multiple organ dysfunction syndrome (MODS) or at risk for developing MODS. The term is intended to include the full spectrum of treatments for this condition, such as administration of the phospholipid nanoparticle compositions of the present application for the purpose of, ameliorating, alleviating or relieving symptoms or complications: delaying the progression of the condition, disease or disorder, curing or eliminating the condition, disease or disorder, and/or reducing the risk of or preventing the condition, disease or disorder, including preventing recurrence of the disease, wherein "preventing" or "prevention" is to be understood to refer to the management and care of a patient for the purpose of hindering the development of the condition, disease or disorder, and includes the administration of the PN compositions to prevent the onset of symptoms or complications. The individual to be treated is a human being. An individual to be treated according to the present application can be of carious ages and/or sexes.

The term "organ failure" refers to an altered organ function in an acutely ill patient requiring medical intervention to achieve body homeostasis and/or to compensate for the loss of function from that failing organ. The organs include but are not limited to heart and vessels (cardiac failure, vascular collapse, hypotension, organ failure), lungs (respiratory failure), liver (liver failure), kidneys (renal failure), brain (encephalopathy).

The term "multiple organ dysfunction syndrome" (abbreviated MODS) refers to pathologically altered function of more than one organ in an acutely ill patient requiring intervention to achieve homeostasis and/or to compensate for the loss of function from the failing organs. The primary cause triggers an uncontrolled inflammatory response. In operative and non-operative patients sepsis is the most common cause. Sepsis may result in septic shock. In the absence of infection a sepsis-like disorder is termed systemic inflammatory response syndrome (SIRS). Both SIRS and sepsis could ultimately progress to MODS. However, in one-third of the patients no primary cause can be found. MODS is well established as the final stage of a continuum ranging from SIRS to sepsis to severe sepsis to MODS it should be noted that MODS is different from reperfusion injury. In reperfusion there is a period of no or low blood flow. When blood flow is restored the reperfusion injury occurs from reactive oxygen species. Scavengers of reactive oxygen species can protect against reperfusion injury. But such scavengers do not protect against MODS. MODS can occur even though blood flow has not been interrupted. The present application provides methods to disarm sepsis and other inducers of MODS. For example: the method of the present application may be used to treat MODS induced by sepsis caused by flu virus or coronavirus (such as SARS. MERS and COVID 19 virus (including variants)) infection, and bacterial, parasitic and fungal infections.

The term "sepsis" is used in the conventional clinical meaning, referring to a whole body inflammatory state (called systemic inflammatory response syndrome (SIRS)) AND the presence of a known or suspected infection. "Severe sepsis" is defined as sepsis-induced organ dysfunction or tissue hypoperfusion (manifesting e.g. as hypotension, elevated lactate, decreased urine output or altered mental status). "Septic shock" is severe sepsis plus persistently low blood pressure despite the administration of intravenous fluids. Sepsis can lead to severe sepsis, septic shock, multiple organ dysfunction syndrome/multiple organ failure (MODS) and death.

The term "systemic inflammatory response syndrome" or "SIRS" is used in the conventional clinical meaning, referring to systemic inflammation in response to an insult without confirmed infectious process. SIRS can be diagnosed when 2 or more of the following criteria are present. 1) Body temperature less than 36° C. (96.8° F.) or greater than 38° C. (100.4° F.); 2) Heart rate greater than 90 beats per minute: 3) Tachypnea (high respiratory rate), with greater than 20 breaths per minute or an arterial partial pressure of carbon dioxide less than 4.3 kPa (32 mmHg); and 4) White blood cell count less than 4000 cells/mm$^3$ ($4 \times 10^9$ cells/L) or greater than 12,000 cells/mm$^3$ ($12=10^9$ cells/L) or the presence of greater than 10% immature neutrophils (band forms). When an infection is suspected or proven (by culture, stain, or polymerase chain reaction (PCR)), together with SIRS, this is per definition sepsis.

The term "systemic inflammation" is altered organ function in an acutely ill patient due to the nonspecific conserved response of the body (vasculature, immune system, tissues) to infections, non-infectious antigens, trauma, burn, organ/tissue destruction/degeneration/damage, ischemia, haemorrhage, intoxication, and: or malignancy.

The terms "micelle" and "lipid carrying micelle (LM)" are used interchangeably herein with reference to an aggregate of molecules dispersed in a liquid, including an aggregate with the hydrophilic "head" regions in contact with surrounding solvent, sequestering the hydrophobic single tail regions in the micelle center, which forms a hydrophobic core suitable for containing and delivering hydrophobic agents.

The term "liposome" as used herein refers to a vesicular structure comprised of a lipids having a tail group comprising a long hydrophobic hydrocarbon chain and a hydrophilic head group. The lipids are arranged to form a lipid bilayer with an inner aqueous core environment suitable for containing and delivering aqueous agents and a lipid wall suitable for containing hydrophobic agents, especially gasses such as oxygen.

Methods of Treatment

One aspect of the present application relates to a method for treating or preventing multiple organ dysfunction syndrome (MODS) in a patient, comprising administering to the subject an effective amount of a PN composition comprising a phospholipid nanoparticle (PN) composition of the present application. The inventors of the present application have unexpectedly found that administration of a PN composition of the present application can prevent or reduce multiple organ dysfunction syndrome (MODS).

The PN compositions of the present application may be used to treat or prevent MODS caused by a plurality of different disease conditions affected by tissue injury, including but not limited to sepsis, major trauma, burns, pancreatitis, aspiration syndromes, extracorporeal circulation (e.g., cardiac bypass), multiple blood transfusion, ischemia-reperfusion injury, autoimmune disease, heat-induced illness, eclampsia, poisoning/toxicity. In some embodiments, the PN compositions of the preset application is used to treat or prevent MODS resulting from sepsis caused by flu virus or coronavirus (such as SARS, MERS and COVID 19 viruses) infection.

In one embodiment, the method comprises administering the PN composition of the present application in an amount effective to provide reversible uptake and release of nitric oxide in the treatment or prevention of MODS. The present application seeks to address the negative consequences associated with nitric oxide (NO) overproduction by providing a PN composition that promotes more effective redistribution of NO. Overproduction of NO causes vasodilation and decreased blood pressure. In patients with MODS or at risk for developing MODS, the responsiveness of the blood to vasopressor medications like Levophed, vasopressin or epinephrine, which constrict the blood vessels and raise blood pressure is markedly decreased.

Nitric oxide synthase (NOS) is the enzyme that catalyzes the conversion of arginine to NO. Previously, an inhibitor of NOS (54C88) was tested in an attempt to reduce the problems caused by the overproduction of NO. However, this trial was terminated early because of increased mortality (Lopez et al., Crit. Care Med. 2004, Vol. 32, No. 1, pp. 21-30). The primary problem with inhibiting NOS is that NO is necessary to maintain vascular patency. Eliminating NO therefore raises blood pressure but also decreases tissue perfusion and promotes organ failure. Another problem with inhibiting NOS is that it plays a role in promoting mitochondria electron transport and ATP production. However, inhibition of NOS is known to decrease mitochondria oxygen consumption rate. ATP production, which can lead to oxidative stress and irreversible impairment of mitochondria.

While not wishing to be bound by theory, it is believed that the PN compositions of the present application comprise a variable reservoir of nitric oxide that may take up or release nitric oxide in a way that varies with local concentrations of nitric oxide so as to provide for more effective management of NO, predicated in part on the fact that both NO and the phospholipid nanoparticle (PN) composition of the present application are hydrophobic.

In this case, NO preferentially localizes in the hydrophobic regions of the PNs relative to the aqueous environment of the blood. FIG. 1 shows the uptake and release of NO in water and the PN composition of the present application as measured by mass spectroscope. The experimental procedure is described in Example 8.

Unlike nitric oxide inhibitors or nitric oxide scavengers that do not release nitric oxide, PN quickly releases nitric oxide that it absorbs. This enables the PN to act as a redistributor of nitric oxide in which it reduces its bioavailability in regions where it is overproduced and releases it to increase the nitric oxide concentration in areas where its concentration is insufficient changing the balance of nitric oxide from one that favors non-survival to one that favors survival. The PN and its analogs can be considered a new class of therapeutics called nitric oxide redistributors as opposed to inhibitors and scavengers.

Accordingly, it is believed that infusion of PNs into the bloodstream allows for the uptake of overproduced NO therein, which can be readily released in areas where the local concentration is deficient. In other words, the PN compositions serve to reduce the bioavailability of NO without affecting its biosynthesis or paracrine autocrine effects. Reduction of overproduced nitric oxide could also reduce the production of peroxy nitrite a highly reactive free radical that is the product of the reaction of nitric oxide with superoxide. In some embodiments, the PN composition is infused to MODS patients to achieve a goal of a mean blood pressure of 60-65 mHg or other suitable blood pressure as needed by the clinical situation.

In some embodiments, the patient receiving PN composition of the present application has been treated or is being treated with a v asopressor (also referred to as vasoactive pharmaceuticals) Examples of vasopressors and vasoactive pharmaceuticals include, but are not limited to. Levophed, vasopressin and epinephrine, Giapreza, phenylephrine, dopamine and dobutamine.

The PN composition of the present application may be administered intravenously, intra-arterially, intraosseously or intracardially to a subject in need of such treatment. In certain embodiments, the PN composition is administered m an amount of 50-5000 ml, 50-4000 ml, 50-3000 ml, 50-2000 ml, 50-1000 ml, 50-500 ml, 100-5000 ml, 100-4000 ml, 100-3000 ml, 100-20010 ml, 100-1000 ml, 100-500 ml, 200-5000 ml, 200-4000 ml, 200-3000 ml, 200-2000 ml, 200-1000 ml, 200-5000 ml, 500-5000 ml, 500-4000 ml, 500-3000 ml, 500-2000 ml, 500-1000 ml, 1000-5000 ml, 1000-40010 ml, 1000-3000 ml and 1000-2000 ml. In some embodiments, the PN composition is administered in an amount equal to about 10%, 15%, 20%, 25%, 30%, 35%, 40%, 45%, 50%, 55% 60%, 65%, 70%, 75%, 80%, 85% or 90% of the normal blood volume of a subject in a period of 30 seconds to 24 hours.

In certain embodiments, the PN composition is given at a rate of 0.1-5000 ml/min, 0.1-2000 ml/min, 0.1-1000 ml/min, 0.1-500 ml/min, 0.1-200 ml/min, 0.1-100 ml/min. 0.1-50 ml/min, 0.1-20 ml/min, 0.1-10 ml/min, 0.1-5 ml/min, 0.1-2 ml/min, 0.1-1 ml/min, 1-5000 ml/min, 1-200 ml/min, 1-1000 ml/min, 1-500 ml/min, 1-200 ml/min, 1-100 ml/min, 1-50 ml/min, 1-20 ml/min, 1-10 ml/min, 1-5 ml/min, 1-2 ml/min, 2-5000 ml/min, 2-2000 ml/min, 2-1000 ml/min, 2-500 ml/min, 2-200 ml min, 2-100 ml/min, 2-50 ml/min, 2-20 ml/min, 2-10 ml/min, 2-5 ml/min, 5-5000 ml/min, 5-2000 ml/min, 5-1000 ml/min, 5-500 ml/min, 5-200 ml/min, 5-100 ml/min, 5-50 ml/min, 5-20 ml/min, 5-10 ml/min, 10-5000 ml/min, 10-4000 ml/min, 10-3000 ml/min, 10-2000 ml/min, 10-1000 ml/min, 10-500 ml/min, 10-200 ml/min, 10-100 ml/min, 10-50 ml/min, 20-5000 ad/min. 20-4000 ml/min, 20-3000 ml/min, 20-2000 ml/min. 20-1000 ml/min, 20.500 ml/min, 20-200 ml/min, 20-101) ml/min, 20-50 ml min. 50-5001) ml/min, 50-4000 ml/min, 50-3000 ml/min, 50-2040 ml/min, 50-1000 ml/min, 50-500 ml/min. 50-200 ml/min, 50-100 ml/min, 100-5000 ml/min, 100-40 (0) ml/mm, 100-3004) ml/min, 100-2000 ml/min, 100-1000 ml/min, 100-500 ml/min, 100-200 ml/min, 200-50410 ml/min, 200-4000 ml/min, 200-3000 ml/min, 200-2000 ml/min, 200-1000 ml/min, 200-500 ml/min, 500-5000 ml/min, 500-4000 ml/min, 5(0-3000 ml/min, 500-2001)

ml/min, 500-1000 ml/min, 1000-5000 ml/min, 1000.4000 nil/mm, 1000-3000 ml/min, 1000-2000 ml/min, 2000-5000 ml/min, 2000-4000 ml/min, 2000-3000) ml/min, 3000-5000 ml/min, 3000-4000 ml/min or 4000-5000 ml, min.

In yet other embodiments, the PN composition is given at a rate of about 500-700 ml/min, 400-800 ml/min or 300-900 ml/min.

In some embodiments, the PN composition is given without oxygenation. In other embodiments, the PN composition is an oxygenated PN composition. In some embodiments, the PN composition is an oxygenated PN composition with an oxygen content of 2-50, 2-40, 2-30, 2-20, 2-10, 2-5, 5-50, 5-40, 5-30, 5-20, 5-10, 10-50, 10-40, 10-30, 10-20, 15-50, 15-40, 15-30, 15-20, 20-50, 20-40, 20-30, 25-50,25-40, 25-30, 30-50, 30-40 or 40-50 ml $O_2$/100 ml PN composition.

Other hemodynamic parameters, such as perfusion of brain, kidneys, heart, muscle, spleen or other tissues, cardiac output, systolic blood pressure, diastolic blood pressure, mean arterial blood pressure, stroke volume index, mitochondria) oxidative phosphorylation followed by near infrared spectroscopy or other means, blood lactate or membrane polarization, may also be used to determine the "effective amount" of the PN composition needed to increase the blood pressure in a subject.

While the PN composition of the present application is being administered to and circulated through the subject, various agents such as cardioplegic or cardiotonic agents may be administered either directly into the subject's circulatory system, administered directly to the subject's myocardium, or added to the PN composition the present application. These components are added to achieve desired physiological effects such as maintaining regular cardiac contractile activity, stopping cardiac fibrillation or completely inhibiting contractile activity of the myocardium or heart muscle.

Cardioplegic agents are materials that cause myocardial contraction to cease and include anesthetics such as lidocaine, procaine and novocaine and monovalent cations such as potassium ion in concentrations sufficient to achieve myocardial contractile inhibition. Concentrations of potassium ion sufficient to achieve this effect are generally in excess of 15 mM.

The Phospholipid Nanoparticle (PN) Composition

In one embodiment, the PN composition for treating or preventing MODS includes a lipophilic or hydrophobic component, one or more amphiphilic emulsifiers, a polar liquid caner; and one or more electrolytes. The amphiphilic emulsifiers form lipophilic or hydrophobic substance-carrying micelles (LMs) having a lipophilic core surrounded by the polar liquid carrier and/or liposomes containing a lipid layer and a hydrophilic interior (or core).

In some embodiments, the PN composition of the present application comprises LMs and liposomes having a diameter of 1-500 nm, 1-400 nm, 1-300 nm or 1-200 nm as determined by electron microscopy.

In some embodiments, the PN composition of the present application comprises (i) LMs having diameters of 30-300 nm, 30-400 nm, 30-300 nm, 30-200 nm, 30-150 nm, 30-120 nm, 30-100 nm, 30-50 nm, 30-50 nm, 30-400 nm, 30-300 nm, 30-200 nm, 30-150 nm, 30-120 nm, 30-100 nm, 30-80 nm, 40-500 nm, 40-400 nm, 40-300 nm, 40-200 nm, 40-150 nm, 40-120 nm, 40-100 nm, 40, 80 nm, 50-500 nm, 50-400 nm, 50-300 nm, 50-200 nm, 50-150 nm, 50-120 nm, 50-100 nm, 50-80 nm, 100-500 nm, 100-400 nm, 10-300 nm, 100-200 nm, 100-150 nm or 100-120 nm as determined by electron microscopy, and (2) liposomes having diameters of 1-30 nm, 1-25 nm, 1-20 nm, 1-15 nm, 1-10 nm, 3-30 nm, 3-25 nm, 3-20 nm, 3-15 nm, 3-10 nm, 5-30 nm, 5-25 nm, 5-20 nm, 5-15 nm, 5-10 nm, 1-30 nm, 7-25 nm, 7-20 nm, 7-15 nm, 7-10 nm, 10-30 nm, 10-25 nm, 10-20 nm or 10-15 nm as determined by electron microscopy.

In some embodiments, the PN composition of the present application comprises nanoparticles (including both micelles and liposomes) having an average particle diameter of 1-100 nm, 1-80 nm, 1-50 nm, 1-40 nm, 1-30 nm, 1-25 nm, 1-20 nm, 1-15 nm, 1-10 nm, 1-5 nm, 5-100 nm, 5-80 nm, 5-50 nm, 5-40 nm, 5-30 nm, 5-25 nm, 5-20 nm, 5-15 nm, 5-10 nm, 10-100 nm, 10-80 nm, 10-50 nm, 10-40 nm, 10-30 nm, 10-25 nm, 10-20 nm, 15-100 nm, 15-80 nm, 15-50 nm, 15-40 nm, 15-30 nm, 15-25 nm, 15-20 nm, 20-100 nm, 20-80 nm, 20-50 am, 20-40 nm, 20-30 nm, 20, 25 nm, 25-100 nm, 25-80 nm, 25-50 nm, 25-40 nm: 25-30 nm, 30-100 nm, 30-80 nm, 30-50 nm, 30-40 nm, 40-101 nm, 40-80 nm, 40-50 nm, 50-100 nm, 50-80 nm, or 80-100 nm as determined by electron microscopy. In some embodiments, the PN composition of the present application comprises nanoparticles having an average particle diameter of 16-18 nm, 15-19 nm or 14-20 nm, as determined b) electron microscopy.

In some embodiments, the PN composition of the present application comprises nanoparticles (including both micelles and liposomes) having an average diameter of 10-300 nm, 10-200 nm, 10-150 nm, 10-120 nm, 10-100 nm, 10-90 nm, 10-70 nm, 10-50 nm, 10-30 nm, 30-300 nm, 30-200 nm, 30-150 nm, 30-120 nm, 30.100 nm, 30-90 nm, 30-70 nm, 30-50 nm, 50-300 nm, 50-200 nm, 50-150 nm, 50-120 nm, 50-100 nm, 50-90 nm, 50-70 nm, 70-300 nm, 70-200 nm, 70-150 nm, 70-120 nm, 70-100 nm, 70-90 nm, 80-3101 nm, 80-200 nm, 80-150 nm, 80-120 nm, 80-100 nm, 80-90 nm, 90-300 nm, 90-200 nm, 90-150 nm, 90-120 nm, 90-100 nm, 100-300 nm, 100-200 nm, 100-150 nm, 100-120 nm, 120-300 nm, 120-200 nm, 120-150 nm, 150-300 nm, 150-210 nm or 2110-300 nm, as determined by dynamic light scattering using e.g., a Malvern Zetasizer model, or nano ZS. In some embodiments, the PN composition of the present application comprises nanoparticles having an average particle diameter of 92.96 nm, 90.98 nm or 85-1015 nm.

The lipophilic or hydrophobic component is dispersed in the polar liquid carrier to form a nanoemulsion that contains single layer micelles with a polar outer surface and an inner hydrophobic space filled with the lipophilic or by hydrophobic component and/or other hydrophobic molecules, and double layer liposomes a polar outer surface and an inner hydrophilic space Because hydrophobic gases, such as oxygen and nitric oxide (NO), preferentially dissolve in the lipid core of the micelles relate % a to water or other aqueous environments, a PN composition of the present application provides the ability, to carry oxygen and other hydrophobic gases to bodily tissues.

The solubility of hydrophobic gases in the lipophilic or hydrophobic core promotes the uptake and transport of these gases to tissues. The endogenously produced gases carbon monoxide, nitric oxide and hydrogen sulfide can also be carried in the emulsion for the modulation of the vascular tone and apoptotic processes.

In some embodiments, the PN composition is an oxygenated PN composition that enhances aerobic metabolism. In some embodiments, the PN composition is an oxygenated PN composition with an oxygen content of 1-50, 1-40, 1-30, 1-20, 1-10, 1-5, 1-2, 2-50, 2-40, 2-30, 2-20, 2-10, 2-5, 5-50, 5-40, 5-30, 5-20, 5-10, 10-50, 10-40, 10-30, 10-20, 15-50, 15-40, 15-30-15-20, 20-50, 20-40, 20-30, 25-50, 25-40,25-30, 30-50, 30-40 or 40-50 ml $O_2$/100 ml PN composition.

In some embodiments, the PN composition comprise NO in an amount of 1-50, 1-40, 1-30, 1-20, 1-10, 1-5, 1-2, 2-50, 2-40, 2-30, 2-20, 2-10, 2-5, 5-50, 5-40, 5-30, 5-20, 5-10, 10-50, 10-40, 10-30, 10-20, 15, 50, 15, 40, 15-30, 15-20, 20, 50, 20-40, 20-30, 25-50, 25-40, 25-30, 30-50, 30-40 or 40-50 ml NO/100 ml PN composition.

Xenon and argon are hydrophobic gases that could provide protection of the brain in pathological states such as seizures. In some embodiments, the PN composition comprise Xe or Ar or both in an amount of 1-50, 1-40, 1-30, 1-20, 1-10, 1-5, 1-2, 2-50, 2-40, 2-30, 2-20, 2-10, 2-5, 5-50, 5-40, 5-30, 5-20, 5-10, 10-50, 10-40, 10-30, 10-20, 15-50, 15-40, 15, 30, 15-20, 20-50, 20-40, 20-30, 25-50, 25-40, 25-30, 30-50, 30-40 or 40-50 ml $O_2$/100 ml PN composition.

In some embodiments, the PN composition of the present application further comprises inhibitors of apoptosis e.g., Z-VAD-FMY, an apoptosis inhibiting peptide), protectors of mitochondria) integrity (e.g., Cyclosporin A, an inhibitor of mitochondria) inner pore opening), modulators of signal transduction, such as diacylglycerol or cyclic GMP, or an antioxidant, such as Coenzyme Q10.

When employing PNs having liposomes with an average diameter below 30 nm, the liposomes can traverse the endothelial cell layer and enter the interstitial space such liposomes may be employed in situations where the permeability of the vascular space has not increased or to promote cellular absorption of lipophilic or hydrophobic mediators or to promote entry of molecules or cellular components that can favorably modulate intracellular mechanisms.

In certain cases, the PN composition of the present application are capable of exerting an osmotic force and absorbing mediators of tissue injury, such as prostaglandin, nitric oxide, leukotrienes, and thromboxane, and other lipophilic or hydrophobic mediators such as platelet actuating factors. Thus, in some cases, the PNs of the present application are able to absorb toxic molecules produced by MODS patients. For example, lymph factors produced in the gut and thoracic duct lymph nodes may result in acute lung injury and red blood cell deformability. Other toxic molecules include, but are not limited to, leukotrienes, prostaglandin, nitric oxide, endotoxin and tumor necrosis factor (TNF). The PNs in the PN composition allow effective absorption of lipophilic or hydrophobic chemical mediators. In other cases, the PNs may be loaded with antagonists to toxic chemical mediators, such as antibodies to endotoxins.

In MODS patients having increased vascular wall permeability caused by e.g. capillary leak, the small size of the above-described phospholipid nanoparticles (PNs) facilitates their entry into interstitial spaces that would be otherwise restricted by larger structures. Capillary leak is caused by the death of endothelial cells and the actions of neutrophils. It is mediated by cytokines such as IL-1 and TNF as well as nitric oxide. Neutrophils adhere to damaged endothelial cells and release reactive oxygen species and cell wall damaging enzymes such as myeloperoxidase. The PNs could get into the interstitium via the capillary leak and provide e.g., an anti-inflammatory effect within the interstitial space.

Preferably the PN compositions are formulated to comprise LMs and/or liposomes that are stable at room temperature (e.g., 25° C.) or 5° C. for a period of at least 3 days, 7 days, two weeks, 4 weeks, 12 weeks, 20 weeks, 180 days, 30 week, 40 weeks, one year or more. Stability may be determined by measuring the change in micelles diameter. An unstable emulsion would have micelles that coalesce and form larger diameter micelles, in certain preferred embodiments, the PN composition is stable for at least 4 weeks at room temperature.

In some embodiments, the PN composition is formed from soybean oil in an amount of 5%-40% (w/v) and lecithin in an in an amount of 1%-18% (w/w). In some embodiments, the PN composition further comprises NaCl at a final concentration of 50-200 mM. In some embodiments, the PN composition further comprises glycerin in an amount of 1-5% In one embodiment, the PN composition comprises 10% (w/v) soybean oil, 0.6% (w/v) egg lecithin, 1.13% (w/v) glycerin and 77 mM NaCl in another embodiment, the PV composition comprises 20% (w/v) soybean oil, 1.2% (w/v) egg lecithin, and 2.25% (w/v) egg lecithin. In another embodiment, the PV composition comprises 20% (w/v) soybean oil, 1.2% (w/v) egg lecithin, and 2.25% (w/v) egg lecithin and 77 mM NaCl.

In some embodiments, the composition is formed from soybean oil in an amount of 10%-40% (w/v), preferably, 15%-35%, lecithin in an in an amount of 6%-18% Otis), preferably 10%45%, sodium chloride and sodium lactate as electrolytes, wherein the total electrolyte composition is between 50 mM to 200 mM, histidine in an amount between 0.1 mN to 10 mM, and water such that the lecithin forms (1) lipid-carrying micelles having a lipophilic or hydrophobic core in an aqueous solution and the resulting micelles have an average diameter between 70-150 nm, preferably between 90 nm and 120 nm, as determined by dynamic light scattering, and are stable for at least 4 weeks at room temperature; and (2) liposomes having a diameter in the range of 1-25 nm, as determined by electron microscopy.

In another embodiment, the PN composition comprises 10-40% (air) soybean oil and 6-18% (w/v) egg lecithin or soybean lecithin. In some embodiments, the PN composition further comprises 0.6% (w/v) NaCl, 0.385% (w/v) Na(L) lactate, and 0.155% (w/v) histidine. In some embodiments, the PN composition comprises 20-30% (w/v) soybean oil, 12% (w/v) egg lecithin or soybean lecithin, 0.6% (w/v) NaCl, 0.385% (w/v) Na(L) lactate, and 0.155% (w/v) histidine.

In another embodiment, the PN composition comprises 20% (w/v) soybean oil, 12% (w/v) egg lecithin or soybean lecithin, 0.6% (w/v) NaCl, 0.385% (w/v) Na(L) lactate, and 0.155% (w/v) histidine, wherein the PN composition is prepared under conditions that form nanoparticles (including liposomes and micelles) with an average diameter of 80-120 nm, as measured by dynamic light scattering. In some embodiments, the nanoparticles comprise liposomes with diameters in the range of 1-25 nm or 7-20 nm, as measured by electronic microscopy and nacelles with diameters in the range of 30-130 nm or 40-100 nm, as measured by electronic microscopy.

In another embodiment, the PN composition comprises 30% (w/v) soybean oil, 12% (w/v) egg lecithin or soybean lecithin, 0.6% (w/v) NaCl, 0.385% (w/v) Na(L) lactate, and 13.155% (w/v) histidine, wherein the PN composition is prepared under conditions that form nanoparticles (including liposomes and micelles) with an average diameter of 80-120 nm, as measured dynamic light scattering. In some embodiments, the nanoparticles comprise liposomes pith diameters in the range of 1-25 nm or 7-20 nm, as measured by electronic microscopy and micelles with diameters in the range of 30-130 nm or 40-100 nm, as measured by electronic microscopy.

Other oils, such as oil from chia beans, pumpkin seeds or other sources ma be used. In certain embodiments, the above described PN composition may further comprise about 2-40% (w/v), about 2-20% (w/v), about 4-10% (w/v), or about 5% (w/v) albumin or albumin polymers or albumin polymers conjugated with amino acids or peptides, which are added to the PN composition after the formation of micelles. In other embodiment the hydrophobic or the hydrophilic component is carried within erythrocyte to ghosts.

In certain embodiments, the LMs make up 10-40% (w/v) of the PN composition, while the liposomes make up 5-30% (w/v) of the PN composition. In some embodiments, the LMs are made using soybean oil and the liposomes are made using chia bean oil, which has a greater anti-inflammatory effect than that of soybean oil.

In certain embodiments the PN composition of the present application comprises a lipophilic or hydrophobic component selected from the group consisting of soybean oil, chia bean oil and algae oil, an emulsifier selected from the group consisting of phospholipids and α-phosphatidylcholine, and an amino acid or n-acetyl amino acid at a final concentration of 0.2-20 mM, 0.5-10 mM, 0.5-5 mM or 0.5-2 mM.

In certain embodiments, the PN composition has a final amino acid concentration of 0.001-10 mM, 0.01-10 mM, 0.1-10 mM, 0.2-10 mM, 0.5-10 mM, 1-10 mM, 2.5-10 mM, 5-10 mM or 7.5-10 mM. In certain embodiments, the PN composition has a final amino acid concentration of 0.001, 0.01, 0.1, 0.2, 0.5, 1.2, 5, 5, 7.5, or 10 mM. The emulsifier:lipophilic or hydrophobic component ratio (w/w) may range between about 1.400 to about 1:1, preferably between about 1:200 to about 1.50 In one embodiment, the emulsifier:lipophilic or hydrophobic component ratio (w/w) is about 1:100. In another embodiment, the emulsifier:lipophilic or hydrophobic component ratio (miss) is about 1.2-100.

In some embodiments, the PN composition substantially consists of liposomes and do not include a lipophilic or hydrophobic component, such as soybean oil.

In some embodiments, the PN composition includes one or more active pharmaceutical ingredients or agents (e.g., nucleic acids, proteins, small molecule drugs etc.) into the LMs and/or liposomes. The active pharmaceutical ingredients or agents can be incorporated into the lipophilic or hydrophobic core of LMs or liposomes or into the hydrophilic core of liposomes.

In one embodiment, the PN composition comprises sod bean oil, egg phospholipids and an amino acid, beta-endorphin or other modulator that acts at femtorpolar concentrations or higher at a final concentration of 0.1 femtomolar (fM) to 10 mM.

The PN compositions of the present application are free of hemoglobin, derivatives of hemoglobin, perfluorocarbon and derivatives of perfluorocarbon. As used herein, a composition is "free of hemoglobin, derivatives of hemoglobin, perfluorocarbon and derivatives of perfluorocarbon" if the composition does not contain any hemoglobin, derivatives of hemoglobin, perfluorocarbon and derivatives of perfluorocarbon, or if the composition contains hemoglobin, derivatives of hemoglobin, perfluorocarbon and derivatives of perfluorocarbon at levels below 0.1% w/v.

The PN compositions of the present application are typically free of $Ca^{++}$, $K^+$, and $Mg^{++}$, and $Al^{+++}$ in certain embodiments. $Ca^{++}$ and $K^+$ are added to the PN composition just prior to use (e.g., within 24 hours prior to use) In other embodiments $Ca^{++}$ is premixed with the PN composition Because $Al^{+++}$ is toxic to bone, brain, hematopoieisis, heme synthesis, globulin synthesis, iron absorption and metabolism, and fetal development, all oils and other components must have the minimum amount of $Al^{+++}$ possible. In certain embodiments, the PN composition contains $Al^{+++}$ at a concentration of less than 25 mg/l, 20 mg/l, 10 mg/l or 5 mg/l. In other embodiments, the PN composition is free of $Al^{+++}$, i.e., undetectable by conventional methods.

In certain embodiments, the micelles in the PN composition of the present application are free-moving micelles that are not encapsulated in any type of particles. Further, the wall of the micelles is comprised of either a single layer or a double layer of the amphiphilic emulsifier molecules so that the micelles may easily merge with the cell membrane of the tissue that comes in contact with the PN composition. Further, the micelles in the PN composition of the present application are free of hemoglobin, derivatives of hemoglobin, perfluorocarbon and derivatives of perfluorocarbon.

Lipophilic or Hydrophobic Component

As used herein, the term "lipophilic component" refers to a fat-soluble material that is naturally occurring, or non-naturally occurring Examples of lipophilic components include but are not limited to, fatty acyls, glycerolipids, phospholipids, sphingolipids, sterol lipids, prenol lipids, saccharolipids, poiyketides, non-natural lipid(s), cationic lipid(s), amphipathic alkyl amino acid derivative, adialkyldimethylammonium, polyglycerol alkyl ethers, polyoxyethylene alkyl ethers, tri-n-octylamine, boric acid, tris(3,5-dimethyl-4-heptyl) ester, triglycerides, diglycerides and other acylglycerols, such as tetraglycerol, pentaglycerol, hexaglycerol, heptaglycerol, octoglycerol, nonaglycol and decaglycerol, hydrophobic peptides, hydrophobic polysaccharides, silicones, lipopeptides, cyclopeptides and mixtures thereof. In certain embodiments, the lipophilic or hydrophobic component comprises soybean oil, chia bean oil or algae oil.

In one embodiment, the lipophilic component is soybean oil. The lipophilic component may also be derived from chia beans that have a high concentration of anti-inflammatory omega 3 fatty acids soybean oil is thrombogenic and procoagulant, and therefore would be preferred when clotting is desired. After bleeding is no longer an issue, oils rich in omega 3 fatty acids would be favored because of their anti-thromobogenic properties. Oils rich in omega 3 fats acids include, but are not limited to chia oil, algae oil, pumpkin oil, flaxseed oil or fish oil.

In certain embodiments, the lipophilic or hydrophobic component comprises an unsaturated fatty acid with one or more alkenyl functional groups in a cis or trans configuration. A cis configuration means that adjacent hydrogen atoms or other groups are on the same side of the double bond. In a trans configuration these moieties are on different sides of the double bond. The rigidity of the double bond freezes its conformation and, in the case of the cis isomer, causes the chain to bend and restricts the conformational freedom of the fatty acid. In general, the more double bonds the chain has, the less flexibility it has. When a chain has many cis bonds, it becomes quite curved in its most accessible conformations. For example, oleic acid, with one double bond, has a "kink" in it, while linoleic acid, with two double bonds, has a more pronounced bend. Alpha-linolenic acid, with three double bonds, favors a hooked shape. The effect of this is that in restricted environments, such as when fatty acids are part of a phospholipid in a lipid bilayer, or triglycerides in lipid droplets, cis bonds limit the ability of fatty acids to be closely packed and therefore could affect the melting temperature of the membrane or of the fat. In some embodiments, the lipophilic or hydrophobic component comprises up to 1%, 2%, 5%, 10%, 15%, 20%, 25%, 30%, 35%, 40%, 45%, 50%, 55%, 60%, 65%, 70%, 75%, 80%, 85%, 90%, 95% or 99% (w/v) unsaturated fatty acid(s) that have one or more alkenyl functional groups in cis configuration.

Examples of cis-unsaturated fatty acids include, but are not limited to, obtusilic acid, linderic acid, tsuzuic acid, palmito-oleic acid, oleic acid, elaidic acid, vaccenic acid, petroselinic acid, gadoletc acid, eicosenoic acid, erucic acid, cetoteic acid, nervonic acid, ximenic acid and lumepueic acid: n-3 type unsaturated fatty acids such as α-linolenic acid, stearidonic acid, eicosatetraenoic acid, etcosapentaenoic acid, docosapentaenoic acid and docosahexaenoic acid, n-6 type unsaturated fatty acids such as linoleic acid, linoelaidic acid, γ-linolenic acid, bis-homo-γ-linolenic acid and arachidonic acid: conjugated fatty acids such as conjugated linoleic acid and α-eleostearic acid: fatty acids carrying double bonds at the 5-position thereof such as pinolenic acid, sciadonic acid, juniperic acid and columbinic acid: polyvalent unsaturated fatty acids, other than those listed above, such as hiragonic acid, moroctic acid, clupanodonic acid and nishinic acid: branched fatty acids such as isobutyric acid, isovaleric acid, iso acid and anti-iso acid: hydroxy fatty acids such as α-hydroxy acid, β-hydroxy acid, mycolic acid and polyhydroxy acid, epoxy-fatty acids: keto-fatty acids, and cyclic fatty acids. In certain embodiments, the lipophilic or hydrophobic component also comprises amphiphilic molecules.

The lipophilic or hydrophobic component may constitute about 1-80%, 1-70-1-60%, 1-50%, 1-40%, 1-30%, 1-20%, 3-80%, 5-70%, 5-60%, 5.50%, 5-40%, 5-30%, 5-20%, 10-80%, 10-70%, 10-60%, 10-50%, 10-40%, 10-30%, 10-20%, 15-80%, 15-70%, 15-60%, 15-50%, 15-40%, 15-30%, 15-20%, 20-80%, 20-70%, 20-60%, 20-50%, 20-40%, 20-30%, 30-80%, 30-70%, 30-60%, 30-50%, 30-40%, 40-80%, 40-70%, 40-60%, 40-50%, 40-80%, 40-70%, 40-60%, 40-30%, 50-80%, 50-70%, 50-60%, 60-80%, 60-70% or 70-80% (w/v) of the PN composition. In certain embodiments, the lipophilic or hydrophobic component constitutes about 10%, about 15%, about 20%, about 25%, about 30% and about 35% (w/v) of the PN composition. In some embodiments, the lipophilic or hydrophobic component comprises between 0-35%, 5-35%, 10-35% 15-35%, 20-35%, 25-35%, 30-35%, 0-30%, 5-30%, 10-30%, 15-30%, 20-30%, 25-30%, 0-25%, 5-25%, 10-25%, 15-25%, 20-25%, 0-15%, 5-15% or 10-15% (w/v) of the PN composition, or any percent range combination comprising integer values selected from the group consisting of 10%, 15%, 20%, 25%, 30% or 35%. In yet other embodiments, the upper limit and/or lower limit of the lipophilic or hydrophobic component is defined by any of the listed concentrations described herein Amphiphilic Emulsifier The amphiphilic emulsifier can be any amphiphile or amphiphilic molecule that will hate its hydrophobic tail in the lipophilic or hydrophobic core of the micelle and its hydrophilic end in contact with the polar carrier. Examples of emulsifiers are egg phospholipids, pure phospholipids, or amphiphilic peptides.

As used herein, the term "amphiphile" refers to a chemical compound possessing both hydrophilic and lipophilic or hydrophobic properties. Examples of amphiphiles include, but are not limited to, naturally-occurring amphiphiles such as phospholipids, cholesterol, glycolipids, fatty acids, bile acids, and saponins, and synthetic amphiphiles such as peptides.

Examples of phospholipids include natural or synthetic phospholipids such as phosphatidylcholine, phosphatidylethanolamine, phosphatidylserine, phosphatidic acid, phosphatidytglycerol, phosphatidylinositol, lisophosphatidylcholine, sphingomyelin, egg yolk, lecithin, soybean lecithin, and a hydrogenated phospholipid.

Examples of the glycolipids include glyceroglycolipids and sphingoglycolipids. Examples of glyceroglycolipids include digalactosyl diglycerides (such as digalactosyl dilauroyl glyceride, digalactosyl dimyristoyl glyceride, digalactosyl dipalmitoyl glyceride, and digalactosyl distearoyl glyceride) and galactosyl diglycerides (such as galactosyl dilauroyl glyceride, galactosyl dimyristoyl glyceride, galactosyl dipalmitoyl glyceride, and galactosyl distearoyl glyceride) Examples of sphingoglycolipids include galactosyl cerebroside, lactosyl cerebroside, and ganglioside.

Examples of the sterols include cholesterol, cholesterol hemisuccinate, 3β-[N—(N', N'-dimethylaminoethane)carbamoyl]cholesterol, ergosterol, and lanosterol.

In one embodiment, the emulsifier comprises egg phospholipid or egg yolk, lecithin. In another embodiment, the emulsifier is soybean lecithin or alpha-phosphatidylcholine.

in other embodiments, the emulsifier may constitute between 0.1-60%, 0.1-50%, 0.1-40%, 0.1-30%, 01.20%, 0.1-15%, 0.1-10%, 0.1-5%, 0.1-2%, 0.3-60%, 0.3-50%, 0.3-40%, 0.3-330%, 0.3-20%, 0.3-15%, 0.3-10%, 0.3-5%, 0.3-2%, 0.6-60%, 0.6-50%, 0.6-50%, 0.6-30%, 0.6-20%, 0.6-15%, 0.6-10%, 0.6-5%, 0.6-2%, 2-60%, 2-50%, 2-40%, 2-30%, 2-20%, 2-15%, 2-10%, 2-5%, 6-60%, 6-50%, 6-40%, 6-30%, 6-20%, 6-15%, 6-10%, 10-60%, 10-50%, 10-40%, 10-30%, 10-20%, 10-15%, 15-60%, 15-50%, 15-40%, 15-30%, 15-20%, 20-60%, 20-50%, 20-40%, 20-30%, 30-60%, 30-50%, 30-40%, 40-60%, 40-50% or 50-60% (w/v) of the PN composition. In certain embodiments, the emulsifier is present at a level of about 6%, about 7%, about 8%, about 9%, about 10%, about 11,%, about 12%, about 13%, about 14%, about 15%, about 16%, about 18%, about 20% (w/v) of the PN composition or any other range between any two of these listed integers. In other embodiments, the emulsifier is present at a level of about 7-9%, 9-11%, 11-13%, 13-15%, 15-17%, 17-19%, 10-14%, 9-15%, or 8-16% (w/v) of the PN composition or any other range between any two of these listed integers. In yet other embodiments, the upper limit and/or lower limit of the emulsifier is defined by any of the listed concentrations described herein.

In certain preferred embodiments, the emulsifier is a lecithin, such as egg yolk lecithin or soybean lecithin in one of the above described amounts or ranges.

Polar Liquid Carrier

The polar liquid carrier can be any pharmaceutically acceptable polar liquid that is capable of forming an emulsion with the lipid. The term "pharmaceutically acceptable" refers to molecular entities and compositions that are of sufficient purity and quality for use in the formulation of a composition or medicament of the present application and that, when appropriately administered to an animal or a human, do not produce an adverse, allergic or other untoward reaction. Since both human use (clinical and over-the-counter) and veterinary use are equally included within the scope of the present application, a pharmaceutically acceptable formulation would include a composition or medicament for either human or veterinary use. In one embodiment, the polar liquid carrier is water or a water based solution. In another embodiment, the polar liquid carrier is a non-aqueous polar liquid such as dimethyl sulfoxide, polyethylene glycol and polar silicone liquids A water-based solution generally comprises a physiologically compatible electrolyte vehicle isosmotic or near isosmotic with whole blood. The carrier can be, for example, physiological saline, a saline-glucose mixture. Ringer's solution, lactated Ringer's solution, Locke-Ringer's solution, Krebs-Ringer's solution, Hartmann's balanced saline, heparinised sodium citrate-citric acid-dextrose solution, and polymeric plasma substitutes, such as polyethylene oxide, polyvinyl pyrrolidone, poly vinyl alcohol and ethylene oxide-propylene glycol condensates. The PN composition may additionally comprise other constituents such as pharmaceutically-acceptable carriers, diluents, fillers and salts, the selection of which depends on the dosage form utilized, the condition being treated, the particular purpose to be achieved according to the determination of the ordinarily skilled artisan in the field and the properties or such additives Electrolytes In one embodiment, the PN composition of the present application includes one or more electrolytes. The electrolyte to be used in the present application typically includes various electrolytes to be used for medicinal purposes Examples of the electrolyte include sodium salts (e.g., sodium chloride, sodium hydrogen carbonate, sodium citrate, sodium lactate, sodium sulfate, sodium dihydrogen phosphate, disodium hydrogen phosphate, sodium acetate, sodium glycerophosphate, sodium carbonate, an amino acid sodium salt, sodium propionate, sodium hydroxybutyrate, and sodium gluconate), potassium salts (e.g., potassium chloride, potassium acetate, potassium gluconate, potassium hydrogen carbonate, potassium glycerophosphate, potassium sulfate, potassium lactate, potassium iodide, potassium dihydrogen phosphate, dipotassium hydrogen phosphate, potassium citrate, an amino acid potassium salt, potassium propionate, and potassium hydroxybutyrate), calcium salts (e.g., calcium chloride, calcium gluconate, calcium lactate, calcium glycerophosphate, calcium pantothenate, and calcium acetate), magnesium salts (e.g. magnesium chloride, magnesium sulfate, magnesium glycerophosphate, magnesium acetate, magnesium lactate, and an amino acid magnesium salt), ammonium salts (e.g., ammonium chloride), zinc salts (e.g., zinc sulfate, zinc chloride, zinc gluconate, zinc lactate, and zinc acetate), iron salts (e.g., iron sulfate, iron chloride, and iron gluconate), copper salts (e.g. copper sulfate), and manganese salts (for example, manganese sulfate). Among those, particularly preferable are sodium chloride, potassium chloride, magnesium chloride, disodium hydrogen phosphate, di potassium hydrogen phosphate, potassium dihydrogen phosphate, sodium lactate, sodium acetate, sodium citrate, potassium acetate, potassium glycerophosphate, calcium gluconate, calcium chloride, magnesium sulfate, and zinc sulfate.

Concentrations of calcium, sodium, magnesium or potassium ions are typically within the range of normal physiological concentrations of such ions in plasma. In general, the desired concentration of these ions is obtained from the dissolved chloride salts of calcium, sodium and magnesium. The sodium ions may also come from a dissolved organic salt of sodium that is also in solution.

In one embodiment, the electrolytes comprise sodium chloride, sodium lactate or both.

In a particular embodiment, the PN composition comprises sodium chloride at a percent concentration of about 0.2-1%, 0.3-0.9%, 0.4-0.8%, 0.5-0.7% or about 0.6% (w/v %).

In another embodiment, the pharmaceutical concentration comprises sodium chloride at a concentration of 50-150 mM, 70-130 mM, 80-120 mM, 90-110 mM, 95-100 mM, or about 97.4 mM.

In another embodiment, the PN composition comprises sodium L-lactate, sodium D-lactate or a mixture thereof at a percent concentration of about 0.1-0.7%, 0.2-0.6%, 0.3-0.5%, 0.35-0.45%, 0.38-0.39% or about 0.385% (w/v).

In another embodiment, the PN composition comprises sodium L-lactate, sodium D-lactate or a mixture thereof at a concentration of 10-60 mM, 20-50 mM, 30-40 mM or about 34 mM.

In one embodiment, the sodium ion concentration is in a range from about 70-180 mM, 90-170 mM, 70-160 mM, 100-160 mM, 110-150 mM, 120-1411 mM, 125-135 mM, 131-133 mM or about 131.4 mM.

In one embodiment, the concentration of calcium ion is in a range of about 0.5-4.0 mM, 0.5-1.0 mM, 0.5-2 mM, 0.5-3 mM, 1-2 mM, 1-3 mM, 1-4 mM, 2-2.5 mM, 2-3 mM, 2-4 mM, 2.5-3 mM or 3-4 mM.

In one embodiment, the concentration of magnesium ion is in a range of 0 to 10 mM, in another embodiment the concentration of magnesium ion is in a range of about 0.3-0.45 mM, 0.3-0.35 mM, 0.3-0.4 mM, 0.35-0.4 mM, 0.35-0.4 mM, 0.35-0.4 mM or 0.4-0.45 mM, it is best not to include excessive amounts of magnesium ion in the PN composition of the invention because high magnesium ion concentrations negatively affect the strength of cardiac contractile activity. In a preferred embodiment of the invention, the solution contains subphysiological amounts of magnesium ion.

In one embodiment, the concentration of potassium ion is in a subphysiological range of between 0-5 mEq/1 K+(0-5 mM), preferably 2-3 mEq/1 K+(2-3 mM). Thus, the PN composition allows for dilution of the potassium ion concentration in stored transfused blood. As a result, high concentrations of potassium ion and potential cardiac arrhythmias and cardiac insufficiency caused thereby can be more easily controlled. The PN composition containing a subphysiological amount of potassium is also useful for purposes of blood substitution and loss temperature maintenance of a subject.

In one embodiment, the concentration of chloride ion is in the range of 50-200 mM, 50-150 mM, 70-180 mM, 70-130 mM, 80-170 mM, 80-120 mM, 90-160 mM, 91-110 mM, 95-150 mM, 95-100 mM, or about 97.4 mM. In another embodiment, the concentration of chloride ion is in the range of 110 mM to 125 mM.

Other sources of ions include sodium salts (e g, sodium hydrogen carbonate, sodium citrate, sodium lactate, sodium sulfate, sodium dihydrogen phosphate, disodium hydrogen phosphate, sodium acetate, sodium glycerophosphate, sodium carbonate, an amino acid sodium salt, sodium propionate, sodium 3-hydroxybutyrate, and sodium gluconate), potassium salts (e.g., potassium acetate, potassium gluconate, potassium hydrogen carbonate, potassium glycerophosphate, potassium sulfate, potassium lactate, potassium iodide, potassium dihydrogen phosphate, dipotassium hydrogen phosphate, potassium citrate, an amino acid potassium salt, potassium propionate, and potassium 3-hydroxybutyrate), calcium salts (e.g., calcium gluconate, calcium lactate, calcium glycerophosphate, calcium pantothenate, and calcium acetate), magnesium salts (e.g., magnesium sulfate, magnesium glycerophosphate, magnesium acetate, magnesium lactate, and an amino acid magnesium salt), ammonium salts, zinc salts (e.g., zinc sulfate, zinc chloride, zinc gluconate, zinc lactate, and zinc acetate), iron salts (e.g., iron sulfate, iron chloride, and iron gluconate), copper salts (e.g. copper sulfate), and manganese salts (for example, manganese sulfate). Among those, particularly preferable are sodium chloride, potassium chloride, magnesium chloride, disodium hydrogen phosphate, dipotassium hydrogen phosphate, potassium dihydrogen phosphate, sodium lactate, sodium acetate, sodium citrate, potassium acetate, potassium glycerophosphate, calcium gluconate, calcium chloride, magnesium sulfate, choline chloride and zinc sulfate.

Gas Carrying Capacity of the PN Composition

The lipophilic or hydrophobic component in the PN composition, in forms such as micelles and/or erythrocyte ghosts provides the ability for the PN composition to carry a larger amount of lipophilic gases than of a purely aqueous solution. Specifically, the lipophilic gases are dissolved into the lipophilic portion of the PN composition to form a homogeneous solution with the lipophilic or hydrophobic component and any other hydrophobic liquid material that may be present in the lipophilic or hydrophobic portion of the PN composition In one embodiment, the lipophilic gas is oxygen. Oxygen is 4.41 times more soluble in lipid than in water (Battion et al., J Amer Oil Chem Soc 1968. 45 830-833). Accordingly, an PN composition with a higher lipid content would be able to carry more oxygen than an PN composition kith a lesser lipid content. In one embodiment, the PN composition has a lipid content of about 1-80% (w/v). In other embodiments, the PN composition has a lipid content of about 10-80% (w/v), 20-60% (w/v), about 20-50% (w/v), about 20-40% (w/v) or about 20-25% (w/v). In set another embodiment, the PN composition has a lipid content of about 21.8%. In certain embodiments, the PN composition is prepared by mixing the lipophilic or hydrophobic component and the polar liquid component in the presence of regular air. In other embodiment, the PN composition is further oxygenated by bubbling regular air or pure oxygen through the PN composition for a desired period of time. Since bubbles are undesirable in the circulation due to the possibility of air embolization a bubble trap would have to be added to remove bubbles leaving only the gas that has been solubilized in the core of the micelle, in the polar carrier or attached to proteins or other additives. The gas may also be loaded onto the micelles by equilibration of the micelles with an atmosphere enriched with the gas combined with gentle movement of the PN composition in a mixture chamber in order to avoid the creation of bubbles. Loading may also be done under pressures greater than 1 atmosphere followed by release of the pressure to allow the release of excess gas.

In another embodiment, the lipophilic gas is xenon (Xe) or argon (Ar). In another embodiment, the lipophilic gas is nitric oxide (NO). In another embodiment, the lipophilic gas is hydrogen sulfide ($H_2S$). In yet another embodiment, the lipophilic gas is carbon monoxide (CO).

In one embodiment, the PN composition contains micelles loaded with a gas mixture (e.g., a mixture of oxygen, hydrogen sulfide, carbon monoxide and/or nitric oxide). In another embodiment, the PN composition contains a mixture of micelles loaded with various gases. For example, the mixture of micelles may contain 50% NO-loaded micelles and 50% $O_2$-loaded micelles.

Rigid Nonplanar Molecules

The PN composition may further comprise molecules with a rigid nonplanar structure. Such molecules will create greater irregularity and more space for gas molecules in the hydrophobic core of the micelle structure, thereby modifying the gas carrying capacity of the micelles. Examples of such molecules include, but are not limited to, (+) naloxone, (+) morphine, and (+) naltrexone.

In one embodiment, molecules with a rigid nonplanar structure is (+) naloxone which, unlike the opiate receptor antagonist (−) naloxone, does not bind to opiate receptor and will not increase pain as (−) naloxone would. In another embodiment, (+) naloxone is used at a concentration of $10^{-5}$-$10^{-4}$ M. In another embodiment, (+) naloxone is used at a concentration of $10^{-4}$ M or higher.

Upon resuscitation, an inflammatory process may be triggered in tissues from patients undergoing conditions that can lead to MODS, including endothelial cell (EC) injury and capillary leak (CL). In sepsis and other diseases, systemic inflammation may be triggered b) the disease and in a similar sequence leads to EC injury and CL. Accordingly, in one embodiment. (+) naloxone is used at a concentration range that produces anti-inflammatory effect at $10^{-5}$-$10^{-4}$ M (Simpkins CO, Ives N. Tate E. Johnson M. Naloxone inhibits superoxide release from human neutrophils (Life Sci 1985 Oct. 14; 37(15): 1381-6).

Molecules with a nonplanar structure also include organic molecules with branched structures Examples of such molecules include, but are not limited to, tri-n-octylamine, tri-n-hexylamine, boric acid, tris(3,5,-dimethyl-4-heptyl) ester, metal complexed and non-metal complexed deuteroporphyrin dimethyl esters and their derivatives, hexaphenylsilole, and silicone polymers.

Plasma Component

The PN composition may further comprise a plasma component. In one embodiment, the plasma is an animal plasma. In another embodiment, the plasma is human plasma. Although not wishing to be bound by any particular scientific theory, it is believed that the administration of blood substitutes may dilute the concentration of coagulation factors to an undesirable level. Accordingly, using plasma as the diluent for the oxygen carrying component avoids this problem. Plasma can be collected by any means known in the art, provided that red cells, white cells and platelets are essentially removed. Preferably, it is obtained using an automated plasmaphoresis apparatus. Plasmaphoresis apparatuses are commercially available and include, for example, apparatuses that separate plasma from the blood by ultrafiltration or by centrifugation. An ultrafitration-based plasmaphoresis apparatus such as manufactured by Auto C, A200 (Baxter International Inc., Deerfield, IL) is suitable because it effectively removes red cells, white cells and platelets while preserving coagulation factors.

Plasma may be collected with an anticoagulant, many of which are well known in the art. Preferred anti-coagulants are those that chelate calcium such as citrate. In one embodiment, sodium citrate is used as an anticoagulant at a final concentration of 0.2-0.5%, preferably 0.3-0.4%, and most preferably at 0.38%. The plasma may be fresh, frozen, pooled and/or sterilized. While plasma from exogenous sources may be preferred, it is also within the present application to use autologous plasma that is collected from the subject prior to formulation and administration of the PN composition.

In addition to plasma from natural sources, synthetic plasma may also be used. The term "synthetic plasma" as used herein, refers to any aqueous solution that comprises at least one plasma protein. Proteins resembling plasma protein may also be used Oncotic Agent In one embodiment, the PN composition further contains an oncotic agent in addition to the lipid micelles. The oncotic agent is comprised of molecules %% hose sire is sufficient to prevent their loss from the circulation by traversing the fenestrations of the capillary bed into the interstitial spaces of the tissues of the body: Examples of oncotic agents include, but are not limited to, dextran (e.g. a love-molecular-weight dextran), dextral derivatives (e g carboxy methyl dextran, carboxdextran, cationic dextran, and dextral, dextran sulfate), hydroxy ethyl starch, hydroxypropyl starch, branched, unsubstituted or substituted starch, gelatin (e.g. modified gelatin), albumin (e.g, human plasma, human serum albumin, heated human plasma protein, and recombinant human serum albumin), PEG, polyvinyl pyrrolidone, carboxymethylcellulose, acacia gum, glucose, a dextrose (e.g., glucose monohydrate), oligosaccharides (e.g., oligosaccharide), a polysaccharide degradation product, an amino acid, and a protein degradation product. Among those, particularly preferable are low-molecular-weight dextran, hydroxyethyl starch, modified gelatin: and recombinant albumin.

Because of its antioxidant effects, albumin may also be used to minimize reactive oxygen species interaction with the components of the micelle and may also stabilize the micelle structure. In one embodiment, the oncotic agent is about 2%, 5%, 7% or 10% (w/v) albumin. In another embodiment, the oncotic agent is a polysaccharide, such as Dextran, in a molecular weight range of 30,000 to 50,000 daltons (D). In yet another embodiment, the oncotic agent is a polysaccharide, such as Dextran, in a molecular weight range of 50,000 to 70,000 D. High molecular weight dextran solutions are more effective in preventing tissue swelling due to their lower rates of leakage from capillaries.

In one embodiment, the concentration of the polysaccharide is sufficient to achieve (when taken together with chloride salts of sodium, calcium and magnesium, organic ion from the organic salt of sodium and hexose sugar discussed above) colloid osmotic pressure approximating that of normal human serum, about 28 mm Hg.

In another embodiment the oncotic agent is glycerol or mannitol in an amount of about 2%, 2.5%, 3%, 3.5%, 4%, 4.5%, 5%, 10%, 15%, 20%, 25% or 30% (w/v) of the PN composition. In other embodiments, PN composition comprises glycerol or mannitol in an amount of 2-5% wk.

Crystalloid Agent

The PN composition may also comprise a crystalloid agent. The crystalloid agent can be any crystalloid which, in the form of the PN composition, is preferably capable of achieving an osmolarity greater than 8041 mOsm/l, i.e. it makes the PN composition "hypertonic" Examples of suitable crystalloids and their concentrations in the PN composition include, but are not limited to, 3%, w/v NaCl, 7% NaCl, 7.5% NaCl, and 7.5% NaCl in 6% w/v dextran. In one embodiment, the PN composition has an osmolarity of between 800 and 2400 mOsm/l.

Anti-inflammatory and immunomodulatory agent

In one embodiment, the PN composition of the present application further includes an anti-inflammatory or immunomodulatory agent. Examples of the anti-inflammatory agent shown to inhibit reactive oxygen species including, but are not limited to, histidine, albumin. (+) naloxone, prostaglandin $D_2$, molecules of the phenylalkylamines class. Other anti-inflammatory compounds and immunomodulatory drug include interferon: interferon derivatives comprising betaseron, β-interferon: prostane derivatives comprising iloprost, cicaprost: glucocorticoids comprising cortisol, prednisolone, methyl-prednisolone, dexamethasone, immunsuppressives comprising cyclosporine A, methoxsalene, sulfasalaiine, azathiopnne, methotrexate; lipoxygenase inhibitors comprising zileuton, MK-886, WY-50295, SC-45662. SC-41661A, B1-L-357; leukotriene antagonists, peptide derivatives comprising ACTH and analogs thereof, soluble TNF-receptors; anti-TNF-antibodies, soluble receptors of interleukins or other cytokines, antibodies against receptors of interleukins or other cytokines, T-cell-proteins; and calcipotriols and analogues thereof taken either alone or in combination.

Carbohydrates and Amino Acids

The PN composition may contain a carbohydrate or a mixture of carbohydrates. Suitable carbohydrates include, but are not limited to, simple hexose (e.g. glucose, fructose and galactose), mannitol, sorbitol or others known to the art. In one embodiment, the PN composition includes physiological levels of a hexose "Physiological levels of a hexose" includes a hexose concentration of between 2 mM to 50 mM. In one embodiment, the PN composition contains 5 mM glucose. At times, it is desirable to increase the concentration of hexose in order to provide nutrition to cells. Thus, the range of hexose may be expanded up to about 50 mM if necessary to provide minimal calories for nutrition.

Other suitable carbohydrates include various saccharides to be used for medicinal purposes. Examples of the saccharides include xylitol, dextrin, glycerin, sucrose, trehalose, glycerol, maltose, lactose, and erythritol.

The PN composition may contain one or more amino acids and/or one or more oligopeptides. Suitable amino acids include, but are not limited to, alanine, arginine, aspartate, asparagine, cysteine, glutamate, glutamine, glycine, histidine, isoleucine, leucine, Ix sine, methionine, phenylanine, proline, serine, threonine, tryptophan, tyrosine, threonine, tryptophan, valine and 2-aminopentanoic acid. In one embodiment, the amino acid is selected from the group consisting of histidine, tyrosine, phenylalanine and cysteine. In another embodiment, the PN composition comprises one or more amino acids known to prevent apoptosis. Examples of such amino acids include glutamine, glycine, proline and 2-aminopentanoic acid.

The amino acid may be used in the concentration range of 0.1 fM-200 mM, 0.1 fM-100 pM, 100 pM-10 nM, 10 nM-10 μM, 0.01-200 mM, 0.2-50 mM, or 0.5-2 mM In one embodiment, the amino acid is used at a concentration of 1 mM.

Buffering Agent

The PN composition of the present application may further comprise a biological buffer to maintain the pH of the fluid at the physiological range of pH7-8. Examples of biological buffers include, but are not limited to, N-2-HYdroxyethylpiperacine-N'-2-hydroxypropanesulfonic acid (HEPES), 3-(N-Morpholino)propanesulfonic acid (MOPS), 2-([2-Hydroxy-1,1-bis(hydroxymethyl)ethyl]amino)glyci ethanesulfonic acid (TES), 3-[N-tris(Hydroxy-methyl)methylamino]-2-hydroxyethyl]-1-piperazinepropanesulfonic acid (EPPS), Tris [hydrolymethyl]-aminoethane (TRAM), and Tris [Hydroxymethyl]methyl aminomethane (TRIS).

In one embodiment, the buffering agent is histidine, imidazole, substituted histidine or imidazole compounds retaining the amphoteric site of the imidazole ring, oligopeptides containing histidine or glycine (such as glygly) or mixtures thereof. Histidine is also capable of reducing reactive oxygen species and inhibiting cell shrinkage (see e.g. Simpkins et al., J Trauma. 2007, 63:565-572). Histidine or imidazole may be used at a concentration of about 1 Mm, 5 Mm, 10 Mm, 20 Mm, 30 Mm, 40 Mm, 50 Mm or in a concentration range of about 0.1 Mm to about 200 Mm, 1 Mm to about 100 Mm, 5 Mm to about 50 Mm, 5 Mm to about 20 Mm or any other range between any of the histidine concentrations listed herein.

In another embodiment, the PN composition of the present application uses normal biological components to maintain in vivo biological Ph. Briefly, some biological compounds, such as lactate, are capable of being metabolized in vivo and act with other biological components to maintain a biologically appropriate pH in an animal. The biological components are effective in maintaining a biologically appropriate pH even at hypothermic temperatures and at essentially bloodless conditions. Examples of the normal biological components include, but are not limited to carboxylic acids, salt and ester thereof. Carboxylic acids have the general structural formula of RCOOX, where R is an alkyl, alkenyl, or aryl, branched or straight chained, containing 1 to 30 carbons which carbons may be substituted, and X is hydrogen or sodium or other biologically compatible ion substituent which can attach at the oxygen position, or is a short straight or branched chain alkyl containing 1-4 carbons, e.g. —CH$_3$—CH$_2$CH$_3$. Examples of carboxylic acids and carboxylic acid salts include, but are not limited to, lactate and sodium lactate, citrate and sodium citrate, gluconate and sodium gluconate, pyruvate and sodium pyruvate, succinate and sodium succinate, and acetate and sodium acetate Coagulation Enhancers Aggressive high volume resuscitation, without controlling the bleeding, can exacerbate the hemorrhage by disrupting the early formed soft thrombi, and diluting coagulation factors. In certain embodiments, the PN composition may further comprise one or more coagulation enhancers. Examples of coagulation factors include, but are not limited to, factor VII, thrombin, platelets and tranexemic acid. These factors may be from natural or non-natural sources. In certain embodiments, factor 7 is added to the PN composition at a concentration of 70-150 IU/kg, prothrombin complex is added to the PN composition at a concentration of 15-40 IU/kg, and fibrinogen is added to the PN composition at a concentration of 50-90 mg/kg. Naturally-derived or synthetic platelets or platelet substitutes may also be added.

Antioxidants

In certain embodiments, the PN composition may further comprise one or more antioxidants Examples of antioxidants include, but are not limited to, sodium hydrogen sulfite, sodium sulfite, sodium pyrosulfite (e.g., sodium metabisulfite), rongalite (CH$_2$OHSO$_2$Na), ascorbic acid, sodium ascorbate, erythorbic acid, sodium erythorbate, cysteine, cysteine hydrochloride, homocysteine, glutathione, thioglycerol, α-thioglycerin, sodium edetate, citric acid, isopropyl citrate, potassium dichloroisocyanurate, sodium thioglycolate, sodium pyrosulfite 1,3-butylene glycol, disodium calcium ethylenediaminetetraacetate, disodium ethylenediaminetetraacetate, an amino acid sulfite (e.g. L-lysine sulfite), butylhydroxyanisole (BHA), butyihydroxytoluene (BHT), propyl gallate, ascorbyl palmitate, vitamin E and derivatives thereof (e.g., dl-α-tocopherol, tocopherol acetate, natural vitamin E, d-δ-tocopherol, mixed tocopherol, and trolox), guaiac, nordihydroguaiaretic acid (NDGA), L-ascorbate stearate esters, soybean lecithin, palmitic acid ascorbic acid, benzotriazol, and pentaerythrityl-tetrakis[3-(3,5-di-t-butyl-4-hydroxyphenyl)propionate] 2-mercaptobenzimidazole. Among those, preferable are sodium hydrogen sulfite, sodium sulfite, ascorbic acid, homocysteine, dl-α-tocopherol, tocopherol acetate, glutathione, and trolox.

Other Components

In addition to the components discussed above, the PN composition may further comprise other additives that include, but are not limited to, antibiotics: such as penicillin, cloxacillin, dicloxacillin, cephalosporin, erythromycin, amoxicillin-clavulanate, ampicillin, tetracycline, trimethoprim-sulfamethoxazole, chloramphenicol, ciprofloxacin, aminoglycoside (e.g., tobramycin and gentamicin), streptomycin, sulfa drugs, kanamycin, neomycin, land monobactams, anti-viral agents, such as amantadine hydrochloride, rimantadin, acyclovir, famciclovir, foscarnet, ganciclovir sodium, idoxuridine, ribavirin, sorivudine, trifluridine, valacyclovir, valgancyclovir, pencycloyvir, vidarabin, didanosine, stavudine, zalcitabine, zidovudine, interferon alpha, and edoxudine, anti-fungal agents such as terbinafine hydrochloride, nystatin, amphotericin B, griseofulvin, ketoconazole, miconazole nitrate, flucytosine, fluconazole, itraconazole, clotrimazole, benzoic acid, salicylic acid, voriconarole, caspofungin, and selenium sulfide, vitamins, amino acids, vessel expanders such as alcohols and poly alcohols, surfactants, antibodies against harmful cytokines such as tumor necrosis factor (TNF) or interleukins, and mediators of vascular potency and immunomoduators, such as prostaglandins, leukotrienes, pro-opiomelanocortin fragments and platelet activating factors.

In certain embodiments, the PN composition may further contain beneficial anions such as lactate or glutamate. Hypertonic lactate containing compositions have been found to be effective in reducing brain edema in patients with acute hemodynamic distress. In one embodiment, the PN composition contains 250 to 2400 Mm of lactic acid or lactate. In another embodiment, the PN composition contains 250 to 2400 Mm of lactic acid or lactate and 2 to 10 Mm potassium.

In certain other embodiments, the PN composition may contain substituted cations. For example, the PN composition may contain choline to substitute sodium ions.

In some other embodiments, the PN composition further comprises a potassium channel blocker, which is capable of inhibiting programmed cell death by preventing potassium efflux.

In certain embodiments, the PN composition further contains anti-cancer drugs and/or intracellular signal molecules, such as Camp and diacylglycerol. In other embodiments, the PN composition further contain one or more organelles or organelle components such as endoplasmic reticulum, ribosomes, and mitochondria in whole or in part.

In other embodiments, the PN composition may be combined with red blood cells, modified red blood cells or other cellular components of blood.

In yet other embodiments, the PN composition further comprises proopiomelanocortin fragments, such as β-endorphin and melanocyte to stimulating hormone, enkephalins or opiates to modify the immune response and to provide analgesia. β-endorphin may also be used at a final concentration of 0.01-100 nm, preferably 0.1-10 nm, more preferably about 1 nm, to modulate neutrophilic function in the septic state (see, e.g., Simpkins et al, J. Natl Med Assoc 1988, 80: 199-203).

In yet other embodiments, the PN composition further comprises one or more neurotropic agents for treatment of psychiatric disease or prevention of psychiatric disease Preparation of the PN Composition The PN composition may be prepared by mixing the lipophilic or hydrophobic component, the emulsifier, the aqueous carrier, and any other components to form an emulsion. Commonly used mixing methods include, but are not limited to, stirring, shaking, homogenization, vibration, microfuidization and sonication.

An exemplary homogenizer is the APV2000 homogenizer (SPX Corporation) Emulsions may be formed at a pressure setting of ~15,000 to 20,000 psi for nanoemulsions <100 nm or ~22.000 to 28,000 psi for larger micelle emulsions of 300 nm. Multiple rounds (cycles) of homogenization may be needed to produce micelles of the desired sizes. The number of homogenization cycles may vary depending upon the formulation and may require, for example, 6-cycles, 8 cycles, 10 cycles, 12 cycles, 15 cycles.

A suitable particle analyzer and/or zeta potential analyzers may be used to evaluate and monitor the size and stability of the micelle compositions. Exemplary analyzers include the Malvern Zetasizer Nano ZS, which can provide both size and zeta potential measurements In one embodiment, the PN composition is formed by mixing a pre-formed lipid emulsion from the above described components with the aqueous carrier. In addition, the PN composition can be carried in erythrocyte ghosts. Specifically, the emulsion should be prepared in manners that allow the lipophilic gases dissolving into the lipophilic or hydrophobic portion of the emulsion but not forming microbubbles which may increase the risk of gas embolization.

In certain embodiments, albumin or albumin polymers or albumin polymers conjugated with amino acids or peptides is added to the PN composition in an amount of 2-40% (w/v), about 2-20% (w/v), about 4-10% (w/v), or about 5% (w/v). The albumin or albumin polymers or albumin polymers conjugated with amino acids or peptides is added to the PN composition after the formation of micelles. In one embodiment, the lipophilic or hydrophobic component, the emulsifier, the aqueous carrier and anyother non-albumin components are mixed to form an emulsion. Albumin, albumin polymers or albumin polymers conjugated with amino acids or peptides is then dissolved in the emulsion at the desired concentration.

In some embodiments. Part A or the mixture of Part A and Part B, is loaded with oxygen, nitric oxide, carbon monoxide, xenon, argon, hydrogen sulfide other hydrophobic gases or mixtures of these gases prior to use. These gases may be used to deliver oxygen for aerobic metabolism after the initial bolus, provide an initial carbon monoxide bolus to protect against MODS, to open vessels in vascular diseases or states involving vascular constriction or obstruction, xenon or argon to protect against the effects of traumatic brain injury or seizures, or hydrogen sulfide to promote long-term tissue preservation. Nitric oxide loaded micelles may also be used as an anti-hypertensive medication. Either Part A, Part B, or the mixture of Part A and Part B can be sterilized by autoclaving.

In some embodiments, the soybean oil, which enhances clotting, is replaced with chia bean oil which is anti-inflammatory and reduces clotting. In one embodiment, a PN composition with soybean oil is used in initial phase of the infusion in which bleeding is occurring A PN composition with chin bean oil is used for later stages of the infusion when bleeding is no longer an issue an issue.

In some other embodiments, the glycerol in Part A is replaced with mannitol. In other embodiments, the egg phospholipids are replaced with α-phosphatidylcholine to eliminate a potential source of protein contamination and anaphylaxis (due to contamination of egg phospholipid with egg protein). In yet other embodiments, the amino acids in Part B of Recipe 2 are replaced with N-acetyl amino acids. In one embodiment, the PN composition is a non-oxygenated PN composition. As used herein, the term "non-oxygenated PN composition" refers to a formulation that is prepared in atmospheric air and is not loaded with oxygen by any oxygenation device or method.

In some embodiments, the PN composition comprises a hydrophillic or hydrophobic component in an amount of 15-35% (w/v), an amphiphilic emulsifier in an amount of 6%-18% (w/v); a polar liquid carrier; and one or more electrolytes, wherein the amphiphilic emulsifier forms lipid carrying micelles (LMs) having a lipophilic or hydrophobic core comprising the lipophilic or hydrophobic component in the polar liquid carrier, and wherein the LMs have diameters in the range of 20-140 nm. In some further embodiments, the PN composition comprises LMs with diameters in the range of 30-140 nm, 30-130 nm, 30-120 nm, 30-100 nm, 30-90 nm, 30-80 nm, 30-70 nm, 40-140 nm, 40-130 nm, 40-120 nm, 40-100 nm, 40-90 nm, 40-80 nm, 50-140 nm, 50-130 nm, 50-120 nm, 50-100 nm, 50-90 nm, 50-80 nm, 50-70 nm, 60-140 nm, 60-130 nm, 60-120 nm, 60-100 nm, 60-90 nm, 60-80 nm, 80-140 nm, 80-130 nm, 80-120 nm, 80-110 nm, 80-100 nm, 100-140 nm, 100-130 nm, 100-120 nm, 100-110 nm, 120-140 nm, 120-130 nm or 130-140 nm, as measured by; electron microscopy method.

In some further embodiments, the PN composition further comprises liposomes with diameters of in the range of 1-30 nm, 1-25 nm, 1-20 nm, 1-15 nm, 1-10 nm, 3-30 nm, 3-25 nm, 3-20 nm, 3-15 nm, 3-10 nm, 5-30 nm, 5-25 nm, 5-20 nm, 5-15 nm, 5-10 nm, 7-30 nm, 7-25 nm, 7-20 nm, 7-15 nm, 7-10 nm, 10-30 nm, 10-25 nm, 10-20 nm, 10-15 nm, 15-30 nm, 15-25 nm, 15-20 nm, 20-30 nm, 20-25 nm or 25-30 nm, as measured by electron microscope.

In some further embodiments, the PN composition comprises nanoparticles (including micelles and liposomes) with an average diameter in the range of about 70-160 nm, 70-150 nm, 70-140 nm, 70.130 run, 70-120 nm, 70-100 nm, 70-90 nm, 80-160 nm, 80-150 nm, 80-140 nm, 80-130 nm, 80-120 nm, 80-110 nm, 80-90 nm, 90-160 nm, 90-150 nm, 90-140 nm, 90-130 nm, 90-120 nm, 90-100 nm, 90-98 nm, 92-96 nm, or 95-140 nm, as measure by dynamic light scattering.

In some embodiments, the PN composition comprises a mixture of LMs with diameters in the range of 30-500 nm and liposomes with diameters in the range of 1-30 nm, as measured by electron microscopy.

In some embodiments, the PN composition comprises a mixture of LMS and liposomes, wherein the average diameter of all particles is in the range of 5-25 nm, 5-20 nm, 5 15 nm, 5-10 nm, 10-25 nm, 10-20 nm, 10-15 nm, 15-25 nm, 15-20 nm or 20-25 nm, as determined by electron microscopy.

In some embodiments, the PN composition comprises about 12% egg lecithin and comprises LMs with diameters of about 30-500 nm and liposomes with diameters of about 1-25 nm, as determined by electron microscopy. In some embodiments, the PN composition comprises about 12% egg lecithin and comprises LMs with diameters of about 40.100 nm and liposomes with diameters of about 7-20 nm, as determined by electron microscopy.

In some embodiments, the PN composition comprises about 5-35% soybean oil and 0.5-20% egg lecithin and comprises LMs with diameters of about 15-800 nm and liposomes with diameters of about 1-300 nm, as determined by electron microscopy.

In some embodiments, the PN composition comprises about 5-25% soybean oil and 0.5-1.5% egg lecithin and comprises LMs with diameters of about 30-400 nm and liposomes with diameters of about 1-150 nm, as determined by electron microscopy.

In some embodiments, the PN composition comprises about 5-25% soybean oil and 0.5-1.5% egg lecithin and comprises LMs with diameters of about 30-400 nm and liposomes with diameters of about 1-150 nm, as determined by electron microscopy.

In some embodiments, the PN composition comprises about 12% egg lecithin and comprises LMs with diameters of about 40-100 nm and Liposomes with diameters of about 7-20 nm, as determined by electron microscopy.

In some embodiments, the PN compositions described above further comprise glycerin in the amount of 1-10%, 1-8%, 1-5%, 1-3%, 1-2%, 5-10%, 2-8%, 2-5%, 2-3%, 3-10%, 3-8%, 3-5%, 5-10%, 5-8% or 8-10% w/v.

In some embodiments, the PN composition described above further comprises NaCl at a final concentration of 50-200 mM, 50-150 mM, or 50-100 mM.

In some embodiments, the PN composition is prepared under atmospheric air without enrichment of oxygen, carbon monoxide, nitric oxide or xenon.

In certain embodiments, the PN composition may be loaded with a lipophilic gas prior to clinical application Examples of such gases include, but are not limited to, oxygen, xenon, argon, nitric oxide, carbon monoxide, hydrogen sulfide the gases are present in amounts sufficient. For regulation of vascular function and cellular embolism. As used herein, "a PN composition loaded with a lipophilic gas" refers to a PN composition that has been subjected to a process to increase the content of such lipophilic gas in the PN composition. A PN composition may be loaded with a lipophilic gas by bubbling the lipophilic gas through the PN composition for a desired period of time, or by agitating the PN composition in the presence of the lipophilic gas under pressure.

In one embodiment, the PN composition is oxygenated by bubbling pure oxygen or a gas with an oxygen content in the range of 21% to 100% (v/v), preferably 40% to 100% (v/v), more preferably 60% to 100% (v/v), and most preferably 80% to 100% (v/v), through the mixture for a period of 30 seconds or longer, preferably 1-15 minutes, more preferably 1-5 minutes. Oxygen may also be added under pressure followed by a reduction of the pressure to one atmosphere. In one embodiment, the PN composition is oxygenated immediately prior to application. The PN composition may be oxygenated using portable oxy gen tanks or portable oxygen concentrators, such the Evergo Portable Pulse Dose Oxygen concentrator produced by Philips Healthcare at Andover, MA.

Another method could be allowing the emulsion to equilibrate with an atmosphere filled with the gas that is to be added. In most cases a bubble trap would be necessary to remove bubbles that could become gas emboli. The equilibration time for a PN composition of a particular composition may be determined experimentally.

In some embodiments, the PN composition comprises an oxygenated lipid emulsion. As used herein, the term "oxygenated lipid emulsion" or "oxygenated PN composition" refers to a specific type of gassed lipid emulsion or gassed fluid which has been forced to absorb oxygen such that the total concentration of oxygen contained therein is greater than that present in the same liquid at atmospheric equilibrium conditions.

EXAMPLES

The following example is put forth so as to provide those of ordinary skill in the art with a complete disclosure and description of how to carry out the method of the present application and is not intended to limit the scope of the invention. Efforts have been made to ensure accuracy with respect to numbers used (e.g., amounts, temperature, etc.), but some experimental error and deviation should be accounted for. Unless indicated otherwise, parts are parts by weight, molecular weight is weight average molecular weight, temperature is in degrees Centigrade, and pressure is at or near atmospheric

Example 1: Preparation of Phospholipid Nanoparticle (PN) Composition

Preparation of Part A
  soy bean oil 10%-20%==10-20 grams
  egg yolk phospholipids 0.6% to 12%=6 to 12 grams
  add water to final volume of 100 ml
  add sodium hydroxide until pH=80
  sonicate to produce phospholipid nanoparticles
Preparation of Part B
  NaCl 0.6 grams
  Na (L) lactate 0.385 grams
  Histidine 0.155 grams
  Part A may be used alone, or mixed with Part B within 24 hours of use, or premixed. Either or both parts may also be lyophilized and water can be added at the time of use. In some embodiments, glycerin was added to the final product at a final concentration of 1.13% (w/v) or 2.25 (w/v).

Example 2: Treatment of MODS in Patient a with the PN Composition

MODS developed in patient A; a 39 year old woman who had a failed heart transplant. Even after the use of ventricular assist devices the patient had a cardiac arrest. Multiple organs had failed. Failure of the lungs was evident by the requirement of 100% oxygen via a ventilator to achieve a viable level of oxygenation. Failure of the heart was demonstrated by the onset of cardiac arrest and the need to inject epinephrine directly into the heart to restore spontaneous contraction. To address the cardiac arrest her chest was opened. The patient had no urine output because of kidney failure. In spite of being on a high dose of Levophed and receiving fluid boluses her mean arterial blood pressure (MAP) was only 43 mmHg. Her lung function was severely impaired as shown by a P/F ratio of only 132. The lower the P/F and the lower the blood pressure the lower the survivability.

The patient a as given 500 ml of the PN composition of the present application over 30 minutes. No other interventions were made. This resulted in improved lung function as shown by an increase in the MAP from 43 mmHg to 69 mmHg. The P/F ratio increased from 132 to 235.

Example 3: Treatment of MODS in Patient B with the PN Composition

Patient B, a 69 year old woman, had an infected foot and developed septic shock which led to MODS. The lungs required ventilator support Kidney function was supported by dialysis. The patient had heart failure after a cardiac arrest. Her MAP was only 39 mmHg in spite of having received boluses of albumin and normal saline and being on extremely high doses of vasopressors which were Levophed at 100 micrograms/minute, vasopressin at 0.1 units/minute and epinephrine at 30 micrograms/minute. In spite of being on a ventilator her P F ratio was only 131.

The patient was given 500 ml of the PN composition of the present application over 30 minutes. Without any additional intervention her MAP increased from 39 to 59 mmHg and her P/F ratio increased from 131 to 240.

Example 4: Treatment of MODS in Patient C with the PN Composition

Patient C was a 65 year old woman who presented to the emergency department with cardiac tamponade due to the accumulation of blood in the pericardial space. This severely limited the expansion of the heart so that it could not deliver sufficient blood flow to the rest of the body. The cardiac tamponade led to two episodes of cardiac arrest and required needle drainage of the blood from the pericardial space. These events led to MODS. After the failure of fluid boluses and oxygen by mask to improve her blood pressure and oxygenation respectively she was placed on a ventilator and vasopressors. Failure of the lungs was seen by a low P/F ratio. Kidney failure was reflected in an increased creatinine. Liver compromise was indicated by an increase in the ratio of aspartate aminotransferase (AST) over the alanine amino transferase (ALT). Poor perfusion of the organs was indicated by an elevated lactate. She was on vasopressors which were, Levophed at 32 micrograms/minute and vasopressin at 0.04 units/minute.

The patient was given 765 ml of the PN composition of the present application over 120 minutes. After the receiving the PN composition her MAP increased from 68 mmHg to 86 mmHg. Her P/F ratio increased from 63 to 116. The Levophed dose was decreased from 32 micrograms/minute to 10 micrograms/minute. Table 1 shows the improvement in her blood laboratory parameters 24 hours after infusion of PN. The decrease in creatinine showed that there was an improvement in kidney function AST is aspartate transaminase and ALT is alanine aminotransferase. Both are enzymes that are in liver tissue. The higher the AST/ALT ration the worse the degree of liver damage. The normal AST/ALT ratio is less than 1.0. The decrease in this ratio after the PN composition is an indicator of improvement in liver function. Lactate is an indicator of overall perfusion of the tissues in the body. The higher the lactate the worse the prognosis. The decreased lactate after infusion of the PN composition is an indicator of improved overall tissue perfusion. The triglyceride level is indicative of the amount of lipid in the blood. After the infusion of the PN composition the triglyceride level increased from 109 and was 736 mg/dL the day after the infusion. Triglyceride level of is an indicator of the change in the level of PN with in the bloodstream over time. No adverse effect of this elevated triglyceride was observed. Twenty-four hours after this elevation the triglyceride level was down to 244 mg/dL.

TABLE 1

Lung function (P/F ratio), kidney function (creatinine), liver compromise (AST/ALT), organ perfusion (lactate) and triglyceride after infusion of PN.

| | Creatinine mg/dL | AST/ALT | Lactate mmol/liter | Triglyceride mg/dL |
|---|---|---|---|---|
| Before infusion of PN (Day 1) | 4.2 | 3.76 | 6.9 | 109 |
| After infusion of 765 ml PN (Day 2) | 3.5 | 1.64 | 3.5 | 736 |

There were no interventions in addition to the infusion of the PN composition during the time of these results. The measurements showed that after the infusion of the PN composition there was improvement in the cardiovascular, pulmonary, renal and hepatic systems. In addition, there was an improvement in overall blood flow through the tissues.

Example 5: Treatment of MODS in Patient D with the PN Composition

Patient D was a 65 year old man with a diagnosis of COVID-19 verified by testing. He had a decrease in MAP that was not reversed by fluids. Vasopressors were necessary to increase his blood pressure to a survivable level. He met the criteria for septic shock when his MAP did not increase after the infusion of fluids. His blood pressure was 68 mmHg even though he was on the vasopressor, Levophed, at 11 micrograms/minute. His pulmonary status severely deteriorated and he was placed on a ventilator In spite of maximum ventilator support his pulmonary status continued to decrease so that his PF ratio was only 56. He was given 200 ml of PN composition over 2.4 hours intravenously. This resulted in an elevation of MAP from 68 mmHg to 78 mmHg. His P/F ratio increased from 56 to 199.

Seven days later while still on the ventilator and receiving Levophed a 5 micrograms minute and vasopressin at 0.04 unites/minute the patient's P/F ratio dropped to 62. The patient was given 200 ml of the PN composition 2.5 hours. This led to an increase in blood pressure from 67 mmHg to 70 mmHg and P/F ratio from 62 to 191.

Six days later the patient was still on the ventilator and on Levophed S micrograms/minute with vasopressin at 0.04 units/minute. The P/F ratio was down to 81. The patient was given 400 ml of the PN composition over 10 minutes. This resulted in an increase in the P/F ratio from 81 to 145. The blood pressure increased so that the patient could be taken completely off of vasopressors. Off the vasopressors the MAP was 107 mmHg.

Example 6: Treatment of MODS in Patient E with the PN Composition

Patient E was a 62 year old man mho was diagnosed with COVID-19 by clinical criteria. He presented before tests for diagnosing COVID-19 were available. He was in septic shock. He also had multifocal pneumonia and a blood culture that was positive for gram positive cocci. For his hypotension he was placed on high dose vasopressors which were Levophed, vasopressin and phenylephrine. In spite of these measures he went into asystolic cardiac arrest. Advanced Cardiac Life Support protocol was followed. But he did not respond. He was given 1000 ml of PN composition. After this his blood pressure increased to 67 mmHg and he was able to be weaned off of vasopressors. His oxygen requirement decreased from 100% inspired oxygen to 55% inspired oxygen.

Example 7: Treatment of MODS in Patient F with the PN Composition

Patient F #15 was a 58 sear old woman with a diagnosis of COVID-19 and septic shock. She had severe pneumonia. She was on a ventilator. In spite of being on high dose vasopressors she went into asystolic cardiac arrest. She did not respond to the Advanced Cardiac Life Support protocol. Her blood pressure was zero until she was given 1000 ml of PN composition. After this infusion her blood pressure rose to a mean of 69 mmHg. Before PN composition her oxygen saturation was 55% in spite of being given inspired oxygen at 100%. After infusion of PN composition her oxygen requirement decreased to 55%.

Example 8: Nitric Oxide Content in Water the PN Composition

Five hundred microliters of PN (containing 20% soybean oil, 1.2% egg lecithin, 2.25% glycerin with a mean particle size of 400 nm by dynamic light scattering) were placed in a 15-mL vial and nitric oxide at 100 ppm in helium was bubbled into the PN for two minutes. The same method was used for the addition of nitric oxide in deionized water. A continuous sampling quadrupole mass spectrometer was used for the quantification of nitric oxide loaded in the sample fluids. The water in the purge vessel was maintained at 37° C., and contained anti foam solution when needed. For the measurement of loaded nitric oxide in PN and water, 100 microliters of sample fluid were injected into the purge vessel of the apparatus. The sample gas was released quickly from the fluid and was transported as a bolus from the purge vessel toward the mass spectrometer. Signals generated by sample gas contact with the detector were integrated using Peakfit (Systat Software Inc., Chicago, Il (USA) and compared with saturation values obtained with deionized water. Ten measurements were made in each group. The volume of nitric oxide taken up was determined as the area under the curs e. The mean values and standard errors were $3.19 \times 10^{-1}$ $0.19 \times 10^{-3}$ and $2.12 \times 10^{-3} \pm 0.17 \times 10^{-3}$ moles per liter for PN and water, respectively; showing that the solubility of NO in 20% PN was 1.5 times that of water. The off-loading of nitric oxide from PN and eater was rapid at approximately 2 seconds each The data obtained are shown in Table 2 below.

TABLE 2

Nitric oxide content in $H_2O$ and PN composition

| | Nitric oxide in Deionized Water ($10^{-3}$ mole/L) | Nitric oxide in 20% PN ($10^{-3}$ mole/L) |
|---|---|---|
| | 2.67 | 2.55 |
| | 1.38 | 2.73 |
| | 2.74 | 2.88 |
| | 2.28 | 2.83 |
| | 1.88 | 3.85 |
| | 2.58 | 3.44 |
| | 1.73 | 2.75 |
| | 1.34 | 4.33 |
| | 1.69 | 3.75 |
| | 2.87 | 2.76 |
| (Mean +/− SE)* | 2.12 ± 0.184 | 3.19 ± 0.193 |

*Two tailed unpaired Student's t test showed significant difference with p = 0.0008

As shown in FIG. 1, compared to water (panel A), PN took up more nitric oxide (panel B). In the representative experiment shown in FIG. 1, the area under the curve correlates with the amount of nitric oxide absorbed and the rate of release of nitric oxide is rapid as is the release from water. This rapid release enables PN to shift the distribution of nitric oxide from nonsurvival to survival.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

What is claimed is:

1. A method for treating multiple organ dysfunction syndrome MODS) in a subject, comprising:
    administering to a subject in need of treatment, an effective amount of a phospholipid (PN) composition comprising:
    a lipophilic or hydrophobic component in an amount of 0-35% (w/v);
    an amphiphilic emulsifier in an amount of at least 0.1% (w/v);
    a polar liquid carrier; and one or more electrolytes,
    wherein the PN composition comprises liposomes and/or micelles having a diameter of 1-800 nm,
    wherein the lipophilic or hydrophobic component is selected from the group consisting of soybean oil, chia bean oil and algae oil.

2. A method for treating multiple organ dysfunction syndrome (MODS) in a subject, comprising:
    administering to a subject in need of treatment, an effective amount of a phospholipid PN) composition comprising:
    a lipophilic or hydrophobic component in an amount of 0-35% (w/v);
    an amphiphilic emulsifier in an amount of at least 0.1% (w/v);
    a polar liquid carrier; and one or more electrolytes,
    wherein the PN composition comprises liposomes and/or micelles having a diameter of 1-800 nm,
    wherein the amphiphilic emulsifier is selected from the group consisting of egg yolk lecithin and soybean lecithin.

3. A method for treating multiple organ dysfunction syndrome MODS) in a subject, comprising:
    administering to a subject in need of treatment, an effective amount of a phospholipid (PN) composition comprising:
    a lipophilic or hydrophobic component in an amount of 0-35% (w/v);
    an amphiphilic emulsifier in an amount of at least 0.1% (w/v);
    a polar liquid carrier; and one or more electrolytes,
    wherein the PN composition comprises liposomes and/or micelles having a diameter of 1-800 nm,
    wherein the non-aqueous polar liquid is selected from the group consisting of dimethyl sulfoxide, polyethylene glycol and polar silicone liquids.

4. A method for treating multiple organ dysfunction syndrome (MODS) in a subject, comprising:
    administering to a subject in need of treatment, an effective amount of a phospholipid (PN) composition comprising:
    a lipophilic or hydrophobic component in an amount of 0-35% (w/v);
    an amphiphilic emulsifier in an amount of at least 0.1% (w/v);
    a polar liquid carrier; and one or more electrolytes,
    wherein the PN composition is an oxygenated PN composition with an oxygen content of 1-50,000 ml $O_2$/100 ml PN composition.

5. A method for treating multiple organ dysfunction syndrome (MODS) in a subject, comprising:
    administering to a subject in need of treatment, an effective amount of a phospholipid (PN) composition comprising:
    a lipophilic or hydrophobic component in an amount of 0-35% (w/v);
    an amphiphilic emulsifier in an amount of at least 0.1% (w/v);
    a polar liquid carrier; and one or more electrolytes,
    wherein the PN composition has an emulsifier:lipophilic or hydrophobic component ratio (w/w) between about 1:200 to about 1:1.7.

6. A method for treating multiple organ dysfunction syndrome (MODS) in a subject, comprising:
    administering to a subject in need of treatment, an effective amount of a phospholipid (PN) composition comprising:
    a lipophilic or hydrophobic component in an amount of 0-35% (w/v);
    an amphiphilic emulsifier in an amount of at least 0.1% (w/v);
    a polar liquid carrier; and one or more electrolytes, wherein the PN composition comprises micelles and liposomes, wherein the micelles in the PN composition have diameters in the range of 30-500 nm as measured by electron microscopy and wherein the liposomes in the PN composition have diameters in the range of 1-30 nm as measured by electron microscopy.

7. A method for treating multiple organ dysfunction syndrome (MODS) in a subject, comprising:
administering to a subject in need of treatment, an effective amount of a phospholipid (PN) composition comprising:
a lipophilic or hydrophobic component in an amount of 0-35% (w/v);
an amphiphilic emulsifier in an amount of at least 0.1% (w/v);
a polar liquid carrier; and one or more electrolytes,
wherein the PN composition comprises liposomes and/or micelles having a diameter of 1-800 nm,
wherein the PN composition has a concentration of magnesium ion in a subphysiological range.

8. A method for treating multiple organ dysfunction syndrome (MODS) in a subject, comprising:
administering to a subject in need of treatment, an effective amount of a phospholipid (PN) composition comprising:
a lipophilic or hydrophobic component in an amount of 0-35% (w/v):
an amphiphilic emulsifier in an amount of at least 0.1% (w/v);
a polar liquid carrier; and one or more electrolytes,
wherein the PN composition comprises liposomes and/or micelles having a diameter of 1-800 nm,
wherein the PN composition further comprises one or more selected from the group consisting of a crystalloid agent, an oncotic agent, an anti-inflammatory agent, an immunomodulatory agent, and a lipophilic gas.

9. A method for treating multiple organ dysfunction syndrome (MODS) in a subject, comprising:
administering to a subject in need of treatment, an effective amount of a phospholipid (PN) composition comprising:
a lipophilic or hydrophobic component in an amount of 0-35% (w/v);
an amphiphilic emulsifier in an amount of at least 0.1% (w/v);
a polar liquid carrier; and one or more electrolytes,
wherein the PN composition comprises liposomes and/or micelles having a diameter of 1-800 nm,
wherein the PN composition further comprises glycerin.

10. A method for treating multiple organ dysfunction syndrome (MODS) in a subject, comprising:
administering to a subject in need of treatment, an effective amount of a phospholipid (PN) composition comprising:
a lipophilic or hydrophobic component in an amount of 0-35% (w/v);
an amphiphilic emulsifier in an amount of at least 0.1% (w/v);
a polar liquid carrier; and one or more electrolytes,
wherein the PN composition comprises liposomes and/or micelles having a diameter of 1-800 nm,
wherein the subject has MODS induced by sepsis caused by COVID 19 virus.

11. A method for treating multiple organ dysfunction syndrome (MODS) due to sepsis in a subject, comprising:
increasing oxygen saturation by administering to a subject in need of treatment, an effective amount of a phospholipid nanoparticle (PN) composition comprising:
a lipophilic or hydrophobic component in an amount of 0-35% (w/v);
an amphiphilic emulsifier in an amount of at least 0.6%;
a polar liquid carrier; and one or more electrolytes,
wherein the micelles in the PN composition have diameters in the range of 30-500 nm as measured by electron microscopy and wherein the PN composition comprises liposomes having a diameter of 1-30 nm.

12. A method for treating multiple organ dysfunction syndrome (MODS) due to sepsis in a subject, comprising:
reducing hypoxia by administering to a subject in need of treatment, an effective amount of a phospholipid nanoparticle (PN) composition comprising:
a lipophilic or hydrophobic component in an amount of 0-35% (w/v);
an amphiphilic emulsifier in an amount of at least 0.6%;
a polar liquid carrier; and one or more electrolytes,
wherein the micelles in the PN composition have diameters in the range of 30-500 nm as measured by electron microscopy and wherein the PN composition comprises liposomes having a diameter of 1-30 nm.

13. A method for treating multiple organ dysfunction syndrome (MODS) in a subject, comprising:
increasing oxygen saturation by administering to a subject in need of treatment, an effective amount of a phospholipid nanoparticle (PN) composition comprising:
a lipophilic or hydrophobic component in an amount of 0-35% (w/v);
an amphiphilic emulsifier in an amount of at least 0.6% (w/v);
a polar liquid carrier; and one or more electrolytes,
wherein the micelles in the PN composition have diameters in the range of 30-500 nm as measured by electron microscopy and wherein the PN composition comprises liposomes having a diameter of 1-30 nm.

* * * * *